(12) United States Patent
Kim

(10) Patent No.: US 6,905,844 B2
(45) Date of Patent: Jun. 14, 2005

(54) HUMAN CERVICAL CANCER 2 PROTOONCOGENE AND PROTEIN ENCODED THEREIN

(76) Inventor: Jin-Woo Kim, Hyundai Apt. 118-804, Apkujung-dong, Kangnam-ku, Seoul (KR), 135-110

( * ) Notice: Subject to any disclaimer, the term of this patent is extended or adjusted under 35 U.S.C. 154(b) by 0 days.

(21) Appl. No.: 10/432,803

(22) PCT Filed: Jul. 9, 2001

(86) PCT No.: PCT/KR01/01172

§ 371 (c)(1),
(2), (4) Date: May 23, 2003

(87) PCT Pub. No.: WO02/44370

PCT Pub. Date: Jun. 6, 2002

(65) Prior Publication Data

US 2004/0029199 A1 Feb. 12, 2004

(30) Foreign Application Priority Data

Nov. 28, 2000 (KR) .......................... 2000-71202

(51) Int. Cl.[7] ................................ C12P 21/06
(52) U.S. Cl. ................ 435/69.1; 435/6; 435/252.3; 435/320.1; 536/23.1; 536/23.5; 536/24.3; 536/24.31
(58) Field of Search ..................... 435/6, 69.1, 252.3, 435/320.1; 536/23.1, 23.5, 24.3, 24.31; 514/44

(56) References Cited

U.S. PATENT DOCUMENTS

| | | | |
|---|---|---|---|
| 5,098,890 A | 3/1992 | Gewirtz | |
| 5,840,708 A | * 11/1998 | Weiss | ............ 514/44 |
| 6,027,905 A | 2/2000 | Wu | |

OTHER PUBLICATIONS

Branch, AD, 1998, TIBS 23: 45–50.*
Gura (Science, 1995, 270:575–577).*
Miller (1995, FASEB J., vol. 9, pp. 190–199).*
Verma (Sep. 1997, Nature, vol. 389, pp. 239–242.*
Crystal (1995, Science, vol. 270, p. 404–410).*
Gura (Science, 1997, 278:1041–1042).*
Jain (Sci. Am., 1994, 271:58–65).*
Curti (Crit. Rev. in Oncology/Hematology, 1993, 14:29–39).*
Hartwell et al (Science, 1997, 278:1064–1068).*
Bishop, J.M., Cell, 64: 235–248 (1991).
Hunter, T., Cell, 64: 249–270 (1991).
Liang, P. and A. B. Pardee, Science, 257: 967–971 (1992.
Kim, J.S., et al., J. Controlled Release, 53: 175–182 (1998).
Kim, JW et al., Gynecol Oncol, 62: 230–240 (1996).
Liang et al. Cancer Res., 52: 6966–6968 (1992).
Miki T et al. Gene, 83: 137–146 (1989).
Hsu et al Histochem Cytochem 29: 577–580 (1989).
Laemmli (Nature, 227: 680–685 (1970).
Sambrook, J. et al., Molecular Cloning: A laboratory manual, New York: Cold Spring Harbor Laboratory (1989), 12.30 to 12.40.
GenBank Accession No. AK000639 (Watanabe, K. et al.) Feb. 22, 2000.
GenBank Accession No. AL050286 (Koehrer, K. et al.) Feb. 18, 2000.

* cited by examiner

*Primary Examiner*—Susan Ungar
*Assistant Examiner*—Minh-Tam Davis
(74) *Attorney, Agent, or Firm*—Anderson Kill & Olick, PC

(57) ABSTRACT

A human cervical cancer 2 protooncogene having a base sequence of SEQ ID: 1 or a fragment thereof is overexpressed in various cancer tissues and can be used in diagnosing various cancers and an anti-sense gene complementary thereto can be used in treating cancers.

12 Claims, 20 Drawing Sheets

SEQUENCE LISTING

<160> NUMBER OF SEQ ID NOS: 6

<210> SEQ ID NO 1
<211> LENGTH: 2003
<212> TYPE: DNA
<213> ORGANISM: Homo sapiens
<220> FEATURE:
<221> NAME/KEY: CDS
<222> LOCATION: (63)..(974)
<220> FEATURE:
<221> NAME/KEY: misc_feature
<222> LOCATION: (321)..(380)
<223> OTHER INFORMATION: single transmembrane domain

<400> SEQUENCE: 1

```
gatggcgctc tccagggtct tcaaagcttc acctttctcc aaaggcagat gtgaagaact        60 tg atg tct tat gtg gta acc aag aca aaa gcg att aat ggg aaa              104
   Met Ser Tyr Val Val Thr Lys Thr Lys Ala Ile Asn Gly Lys
     1               5                  10 tac cat cgt ttc ttg ggt cgt cat ttc ccc cgc ttc tat gtc ctg tac        152
Tyr His Arg Phe Leu Gly Arg His Phe Pro Arg Phe Tyr Val Leu Tyr
 15                  20                  25                  30 aca atc ttc atg aaa gga ttg cag atg tta tgg gct gat gcc aaa aag        200
Thr Ile Phe Met Lys Gly Leu Gln Met Leu Trp Ala Asp Ala Lys Lys
                 35                  40                  45 gct aga aga ata aag aca aat atg tgg aag cac aat ata aag ttt cat        248
Ala Arg Arg Ile Lys Thr Asn Met Trp Lys His Asn Ile Lys Phe His
             50                  55                  60 caa ctt cca tac cgg gag atg gag cat ttg aga cag ttc cgc caa gac        296
Gln Leu Pro Tyr Arg Glu Met Glu His Leu Arg Gln Phe Arg Gln Asp
         65                  70                  75 gtc acc aag tgt ctt ttc cta ggt att att tcc att cca cct ttt gcc        344
Val Thr Lys Cys Leu Phe Leu Gly Ile Ile Ser Ile Pro Pro Phe Ala
     80                  85                  90 aac tac ctg gtc ttc ttg cta atg tac ctg ttt ccc agg caa cta ctg        392
Asn Tyr Leu Val Phe Leu Leu Met Tyr Leu Phe Pro Arg Gln Leu Leu
 95                 100                 105                 110 atc agg cat ttc tgg acc cca aaa caa caa act gat ttc tta gat atc        440
Ile Arg His Phe Trp Thr Pro Lys Gln Gln Thr Asp Phe Leu Asp Ile
                115                 120                 125 tat cat gct ttc cgg aag cag tcc cac cca gaa att att agt tat tta        488
Tyr His Ala Phe Arg Lys Gln Ser His Pro Glu Ile Ile Ser Tyr Leu
            130                 135                 140 gaa aag gtc atc cct ctc att tct gat gca gga ctc cgg tgg cgt ctg        536
Glu Lys Val Ile Pro Leu Ile Ser Asp Ala Gly Leu Arg Trp Arg Leu
        145                 150                 155 aca gat ctg tgc acc aag ata cag cgt ggt acc cac cca gca ata cat        584
Thr Asp Leu Cys Thr Lys Ile Gln Arg Gly Thr His Pro Ala Ile His
    160                 165                 170 gat atc ttg gct ctg aga gag tgt ttc tct aac cat cct ctg ggc atg        632
Asp Ile Leu Ala Leu Arg Glu Cys Phe Ser Asn His Pro Leu Gly Met
175                 180                 185                 190 aac caa ctc cag gct ttg cac gtg aaa gcc ttg agc cgg gcc atg ctt        680
Asn Gln Leu Gln Ala Leu His Val Lys Ala Leu Ser Arg Ala Met Leu
                195                 200                 205 ctc aca tct tac ctg cct cct ccc ttg ttg aga cat cgt ttg aag act        728
Leu Thr Ser Tyr Leu Pro Pro Pro Leu Leu Arg His Arg Leu Lys Thr
            210                 215                 220 cat aca act gtg att cac caa ctg gac aag gct ttg gca aag ctg ggg        776
His Thr Thr Val Ile His Gln Leu Asp Lys Ala Leu Ala Lys Leu Gly
```

```
                225                 230                 235
att ggc cag ctg act gct cag gaa gta aaa tcg gct tgt tat ctc cgt     824
Ile Gly Gln Leu Thr Ala Gln Glu Val Lys Ser Ala Cys Tyr Leu Arg
    240                 245                 250 ggc ctg aat tct acg cat att ggt gaa gat agg tgt cga act tgg ctg     872
Gly Leu Asn Ser Thr His Ile Gly Glu Asp Arg Cys Arg Thr Trp Leu
255                 260                 265                 270 gga gaa tgg ctg cag att tcc tgc agc ctg aaa gaa gct gag ctg tct     920
Gly Glu Trp Leu Gln Ile Ser Cys Ser Leu Lys Glu Ala Glu Leu Ser
                275                 280                 285 ctc ttg ctg cac aac gtg gtc ctg ctc tcc acc aac tac ctt ggg aca     968
Leu Leu Leu His Asn Val Val Leu Leu Ser Thr Asn Tyr Leu Gly Thr
                290                 295                 300 agg cgc       tgaatg aaccatggag cggatggcat tgtcctgcag tcgtatagta   1020
Arg Arg tagcagtgca ggaacaaaca gcacttgcca gcaaagtctg tgtgtactgt taagtgtgtg   1080
ggaggcagag agaggagcag ggccatgggc cttcacagca tggcacacct gtgggaactg   1140
cagacattcc tctcacagct agaactgaaa caaaccctct gctaggggt ggtccgtgtg   1200 aggtgtcatc ctgtccccct cataattact aatagctgga actggcagca gcctctactg   1260
ggcttttact gtgatgtgtt cagttcatgt cctaggaagt cagcttttgc cccaggtggg   1320
aatccttatt tggcttagga ctgatccact tccatgttac ttacatctgt gggttttgt    1380 tgttgctgtt agaaaatttt tggctggtga aacagcact cctttggctg gagcacttgt   1440
gtccatgcat gtacttgggt gtttccctcc atcctttctg atatgaccaa aaatcaagtt   1500
gttttgtttt ttgtcacctt cactggcatg ggctaaccac ttcttttca accctctga    1560 acaccttttt ctgatgggta acttgcagga atattctatt ggaaaagata acaggaagta   1620
caagtgcttc ttgaccccctt cctcaatgtt tctagccttc actctccatt gtcttttctg  1680
ggctgtatta cagccctctg tggatcttca actctgctgc ctccactgtg atgcagcagt   1740
ccaactgtaa ctgacagtgg ctgccttctc tgggccatgg atcacacctg taaggtacta   1800
attactgccc agcctgggga gatcaggaga ggtctgcata gttagtaagt tgggtttagc   1860
ttttgtgtgt gcatcagtga cttagagttc tgtaataact tattgtaaat gcatgaagca   1920
ctgtttttaa acccaagtaa agactgcttg aaacctgttg atggaaaaaa aaaaaaaaaa   1980
aaaaaaaaaa aaaaaaaaaa aaa                                           2003
```

<210> SEQ ID NO 2
<211> LENGTH: 304
<212> TYPE: PRT
<213> ORGANISM: Homo sapiens

<400> SEQUENCE: 2

```
Met Ser Tyr Val Val Thr Lys Thr Lys Ala Ile Asn Gly Lys Tyr His
1               5                   10                  15

Arg Phe Leu Gly Arg His Phe Pro Arg Phe Tyr Val Leu Tyr Thr Ile
            20                  25                  30

Phe Met Lys Gly Leu Gln Met Leu Trp Ala Asp Ala Lys Lys Ala Arg
        35                  40                  45

Arg Ile Lys Thr Asn Met Trp Lys His Asn Ile Lys Phe His Gln Leu
    50                  55                  60

Pro Tyr Arg Glu Met Glu His Leu Arg Gln Phe Arg Gln Asp Val Thr
65                  70                  75                  80

Lys Cys Leu Phe Leu Gly Ile Ile Ser Ile Pro Pro Phe Ala Asn Tyr
```

```
                85                  90                  95
Leu Val Phe Leu Leu Met Tyr Leu Phe Pro Arg Gln Leu Leu Ile Arg
            100                 105                 110
His Phe Trp Thr Pro Lys Gln Gln Thr Asp Phe Leu Asp Ile Tyr His
            115                 120                 125
Ala Phe Arg Lys Gln Ser His Pro Glu Ile Ile Ser Tyr Leu Glu Lys
            130                 135                 140
Val Ile Pro Leu Ile Ser Asp Ala Gly Leu Arg Trp Arg Leu Thr Asp
145                 150                 155                 160
Leu Cys Thr Lys Ile Gln Arg Gly Thr His Pro Ala Ile His Asp Ile
                165                 170                 175
Leu Ala Leu Arg Glu Cys Phe Ser Asn His Pro Leu Gly Met Asn Gln
            180                 185                 190
Leu Gln Ala Leu His Val Lys Ala Leu Ser Arg Ala Met Leu Leu Thr
            195                 200                 205
Ser Tyr Leu Pro Pro Leu Arg His Arg Leu Lys Thr His Thr
            210                 215                 220
Thr Val Ile His Gln Leu Asp Lys Ala Leu Ala Lys Leu Gly Ile Gly
225                 230                 235                 240
Gln Leu Thr Ala Gln Glu Val Lys Ser Ala Cys Tyr Leu Arg Gly Leu
                245                 250                 255
Asn Ser Thr His Ile Gly Glu Asp Arg Cys Arg Thr Trp Leu Gly Glu
                260                 265                 270
Trp Leu Gln Ile Ser Cys Ser Leu Lys Glu Ala Glu Leu Ser Leu Leu
                275                 280                 285
Leu His Asn Val Val Leu Leu Ser Thr Asn Tyr Leu Gly Thr Arg Arg
            290                 295                 300

<210> SEQ ID NO 3
<211> LENGTH: 13
<212> TYPE: DNA
<213> ORGANISM: Artificial Sequence
<220> FEATURE:
<223> OTHER INFORMATION: arbitrary primer

<400> SEQUENCE: 3
aagctttctc tgg                                                          13

<210> SEQ ID NO 4
<211> LENGTH: 16
<212> TYPE: DNA
<213> ORGANISM: Artificial Sequence
<220> FEATURE:
<223> OTHER INFORMATION: H-T11G anchored oligo-dT primer

<400> SEQUENCE: 4 aagtttttt tttttg                                                        16

<210> SEQ ID NO 5
<211> LENGTH: 16
<212> TYPE: DNA
<213> ORGANISM: Artificial Sequence
<220> FEATURE:
<223> OTHER INFORMATION: H-T11C anchored oligo-dT primer

<400> SEQUENCE: 5
aagctttttt tttttc                                                       16

<210> SEQ ID NO 6
```

-continued

```
<211> LENGTH: 16
<212> TYPE: DNA
<213> ORGANISM: Artificial Sequence
<220> FEATURE:
<223> OTHER INFORMATION: H-T11A anchored oligo-dT primer

<400> SEQUENCE: 6
aagctttttt ttttta                                              16
```

HUMAN CERVICAL CANCER 2 PROTOONCOGENE AND PROTEIN ENCODED THEREIN

This application is a national stage 371 application of PCT/KR01/01172, filed on Jul. 9, 2001, which claims benefit from application Republic of Korea 2000-71202 filed on Nov. 28, 2000.

FIELD OF THE INVENTION

The present invention relates to a novel protooncogene and protein encoded therein, and more particularly, to a human cervical cancer 2 protooncogene and a protein derived therefrom, which can be used in diagnosis of various cancers.

BACKGROUND OF THE INVENTION

Higher animals including man each carry approximately 100,000 genes, but only about 15% thereof is expressed, and characteristics of individual's biological process, e.g., genesis, differentiation, homeostasis, responses to stimuli, control of cell segmentation, aging and apoptosis (programmed cell death), are determined depending on which genes are expressed(see Liang, P. and A. B. Pardee, *Science*, 257: 967–971(1992)).

Pathogenic phenomena such as tumorigenesis are caused by gene mutation which brings about changes in the mode of gene expression. Therefore, comparative studies of gene expressions in various cells have been conducted to provide bases for establishing viable approaches to the understanding of diverse biological phenomena.

For example, the mRNA differential display(DD) method suggested by Liang and Pardee is effective in elucidating the nature of tumor suppressor genes, cell cycle-related genes and transcriptional regulatory genes that control apoptosis (see Liang, P. and A. B. Pardee supra). Further, the DD method has been widely used in examining the interrelationship of various genes in a cell.

It has been reported that tumorigenesis is caused by various genetic changes such as the loss of chromosomal heterozygosity, activation of oncogenes and inactivation of tumor suppressor genes, e.g., p53 gene(see Bishop, J. M., *Cell*, 64: 235–248(1991); and Hunter, T., *Cell*, 64: 249–270 (1991)). Further, it has been reported that 10 to 30% of human cancer arises from the activation of oncogene through amplification of protooncogenes.

Therefore, the activation of protooncogenes plays an important role in the etiology of many tumors and there has existed a need to identify protooncogenes.

The present inventor has endeavored to unravel examine the mechanism involved in the tumorigenesis of cervical cancer; and, has unexpectedly found that a novel protooncogene, human cervical cancer 2(HCCR-2), is specifically overexpressed in cancer cells. This protooncogene can be effectively used in diagnosis, prevention and treatment of various cancers, e.g., leukemia, lymphoma, colon, breast, kidney, stomach, lung, ovary and uterine cervix cancers.

SUMMARY OF THE INVENTION

Accordingly, the primary object of the present invention is to provide a novel protoncogene and a fragment thereof.

Other objects of the present invention are to provide:

a recombinant vector containing said protooncogene or a fragment thereof and a microorganism transformed therewith;

a protein encoded in said protooncogene and a fragment thereof;

a kit for diagnosis of cancer containing said protooncogene or a fragment thereof;

a kit for diagnosis of cancer containing said protein or a fragment thereof;

an anti-sense gene having a base sequence complementary to that of said protooncogene or a fragment thereof; and a process for treating or preventing cancer by using said anti-sense gene.

In accordance with one aspect of the present invention, there is provided a novel protooncogene having the nucleotide sequence of SEQ ID No:1 or a fragment thereof.

In accordance with another aspect of the present invention, there is provided a recombinant vector containing said protooncogene or a fragment thereof and a microorganism transformed with said vector.

In accordance with still another aspect of the present invention, there is provided a protein having the amino acid sequence of SEQ ID No:2 or a fragment thereof derived from said protooncogene or a fragment thereof.

BRIEF DESCRIPTION OF THE DRAWINGS

The above and other objects and features of the present invention will become apparent from the following description of the invention, when taken in conjunction with the accompanying drawings which respectively show.

DETAILED DESCRIPTION OF THE INVENTION

Figure 1:
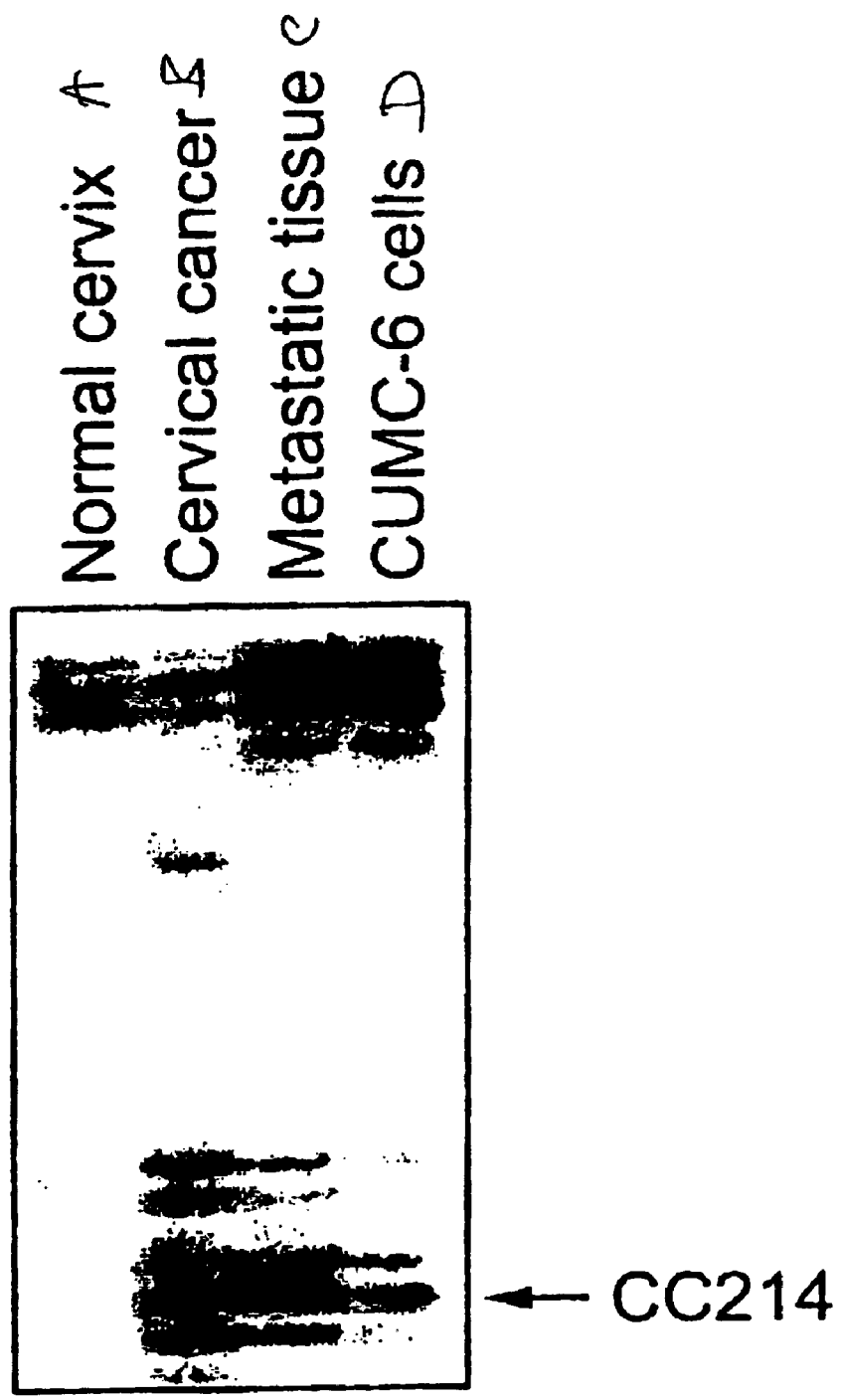
FIG. 1: the DD identification of altered gene expression in normal cervix tissue, primary cervical cancer tissue, metastatic lymph node tissue and cervical cancer cell line (CUMC-6)

The novel protooncogene of the present invention, i.e., human cervical cancer 2(hereinafter "HCCR-2 protooncogene"), consists of 2003 base pairs and has the DNA sequence of SEQ ID NO:1.

In SEQ ID NO: 1, the full open reading frame corresponding to base Nos. 63 to 977 is a protein encoding region and the predicted amino acid sequence derived therefrom is shown in SEQ ID NO: 2 which consists of 304 amino acids("HCCR-2 protein"). Further, the region represented by nucleotide No. 321 to 380 of SEQ ID NO: 1 encodes a single transmembrane domain having the predicted amino acid sequence of amino acid Nos. 87 to 106 of SEQ ID NO: 2. This suggests that the protooncogene of the present invention is a membrane-bound gene.

A single potential N-glycosylation site(corresponding to base Nos. 831 to 839 of SEQ ID NO: 1 and amino acid Nos. 257 to 259 of SEQ ID NO: 2) is present at the C-terminal side of the HCCR-2 protein, which suggests that HCCR-2 is a type II membrane protein. The polyadenylation signal corresponds to the nucleotide Nos. 1894–1898 of SEQ ID NO: 1.

In consideration of the degeneracies of codons and the preferred codons in a specific animal wherein the protooncogene of the present invention is to be expressed, various changes and modifications of the DNA sequences of SEQ ID NO:1 may be made, e.g., in the coding area thereof without adversely altering the amino acid sequence of the expressed protein, or in the non-coding area without adversely affecting the expression of the protooncogene. Therefore, the present invention also includes, in its scope, a polynucleotide having substantially the same base sequence as the inventive protooncogene, and a fragment thereof. As used herein, "substantially the same polynucleotide" refers to a polynucleotide whose base sequence shows 80% or more, preferably 90% or more, most preferably 95% or more homology to the protooncogene of the present invention.

The protein expressed from the protooncogene of the present invention consists of 304 amino acids and has the amino acid sequence of SEQ ID NO: 2. The molecular weight of this protein is about 45 kDa. However, various substitution, addition and/or deletion of the amino acid residues of protein may be performed without adversely affecting the protein's function. Further, a portion of the protein may be used when a specific purpose is to be fulfilled. These modified amino acids and fragments thereof are also included in the scope of the present invention. Therefore, the present invention includes, in its scope, a polypeptide having substantially the same amino acid sequence as the protein derived from the oncogene of the present invention and a fragment thereof. As used herein, "substantially the same polypeptide" refers to a polypeptide whose amino acid sequence shows 80% or more, preferably 90% or more, most preferably 95% or more homology to the amino acid sequence of SEQ ID NO: 2.

The protooncogene, or the protein, of the present invention can be obtained from human cancer tissues or synthesized using a conventional DNA or peptide synthesis method. Further, the gene thus prepared may be inserted to a conventional vector to obtain an expression vector, which may, in turn, be introduced into a suitable host, e.g., a microorganism such as an *E. coli* or yeast, or an animal cell such as a mouse or human cell.

The transformed host may then be used in producing the inventive DNA or protein on a large scale. For example, *E. coli* JM109 is transformed with expression vector pCEV-LAC (Miki, T. et al., *Gene*, 83: 137–146 (1989)) containing the inventive HCCR-2 gene (designated HCCR-2/pCEV-LAC) to obtain an *E. coli* transformant designated JM109/HCCR2 which was deposited on Oct. 11, 1999 with the Korean Collection for Type Cultures(KCTC)(Address: Korea Research Institute of Bioscience and Biotechnology (KRIBB), #52, Oun-dong, Yusong-ku, Taejon, 305–333, Republic of Korea) under the accession number, KCTC 0668BP, in accordance with the terms of Budapest Treaty on the International Recognition of the Deposit of Microorganism for the Purpose of Patent Procedure.

In preparing a vector, expression-control sequences, e.g., promoter. terminator, self replication sequence and secretion signal, are suitably selected depending on the host cell used.

The overexpression of the protooncogene of the present invention occurs not in normal cervical tissue but in cervical cancer tissues and cervical cancer cell lines. This suggests that the protooncogene of the present invention induces cervical cancer. Further, when a normal fibroblast cell, e.g., NIH/3T3 cell line, is transfected with the protooncogene of the present invention, an abnormal cells is produced. Morphological characterizations with optical and electronic microscopes show that the abnormal cell has the form of a tumor cell.

When the normal fibroblast cell transfected with the protooncogene of the present invention is injected into the posterial lateral aspect of a nude mouse, tumorigenesis is observed after about 21 days from the injection, the tumor size becoming 1 cm×1 cm in 40 days. By using hematoxylin-eosin dye method, it can be confirmed that the tumor cells are cancerous.

In addition to epithelial tissues such as cervical cancer tissue, the overexpression of the protooncogene of the present invention is also observed in various other cancer tumors such as leukemia, lymphoma, breast, kidney, ovary, lung and stomach cancers. Therefore, the protooncogene of the present invention is believed to be a factor common to all forms of various cancer and it can be advantageously used in the diagnosis of various cancers and the production of a transformed animal as well as in an anti-sense gene therapy.

A diagnostic method that can be performed using the protooncogene of the present invention may comprise, for example, the steps of hybridizing nucleic acids separated from the body fluid of a subject with a probe containing the protooncogene of the present invention or a fragment thereof, and determining whether the subject has the protooncogene by using a conventional detection method in the art. The presence of the protooncogene may be easily detected by labeling the probe with a radioisotope or an enzyme. Therefore, a cancer diagnostic kit containing the protooncogene of the present invention or a fragment thereof is also included in the scope of the present invention.

A transformed animal produced by introducing the protooncogene of the present invention into a mammal, e.g., a rat, is also included in the scope of the present invention. In producing such a transformed animal, it is preferred to introduce the inventive protooncogene to a fertilized egg of an animal before the 8th cell cycle stage. The transformed animal can be advantageously used in screening for carcinogens or anticancer agents such as antioxidants.

The present invention also provides an anti-sense gene which is useful in a gene therapy. As used herein, the term "an anti-sense gene" means a polynucleotide comprising a base sequence which is fully or partially complementary to the sequence of the mRNA which is transcribed from the protooncogene having the base sequence of SEQ ID NO: 1 or a fragment thereof, said nucleotide being capable of preventing the expression of the open reading frame(ORF) of the protooncogene by way of attaching itself to the protein-binding site of mRNA.

The present invention also includes within its scope a process for treating or preventing cancer in a subject by way of administering a therapeutically effective amount of the inventive anti-sense gene thereto.

In the inventive anti-sense gene therapy, the anti-sense gene of the present invention is administered to a subject in a conventional manner to prevent the expression of the protooncogene. For example, the anti-sense ODN is mixed with a hydrophobized poly-L-lysine derivative by electrostatic interaction in accordance with the method disclosed by Kim, J. S. et al.(*J. Controlled Release*, 53: 175–182(1998)) and the resulting mixed anti-sense ODN is administered intravenously to a subject.

The present invention also includes within its scope an anti-cancer composition comprising the anti-sense gene of the present invention as an active ingredient, in association with pharmaceutically acceptable carriers, excipients or other additives, if necessary. The pharmaceutical composition of the present invention is preferably formulated for administration by injection.

The amount of the anti-sense gene actually administered should be determined in light of various relevant factors including the condition to be treated, the chosen route of administration, the age and weight of the individual patient, and the severity of the patient's symptoms.

The protein expressed from the inventive protooncogene may be used in producing an antibody useful as a diagnostic tool. The antibody of the present invention may be prepared in the form of a monoclonal or polyclonal antibody in accordance with any of the methods well known in the art by using a protein having the amino acid sequence of SEQ ID NO: 2 or a fragment thereof. Cancer diagnosis may be carried out using any of the methods known in the art, e.g., enzyme linked immunosorbentassay(ELISA), radioimmunoassay(RIA), sandwich assay, immunohistochemical staining, western blot or immunoassay blot on polyacrylic gel, to asses whether the protein is expressed in the body fluid of the subject. Therefore, a cancer diagnostic kit containing the protein having the amino acid sequence of SEQ ID NO: 2 or a fragment thereof is also included in the scope of the present invention.

A continuously viable cancer cell line may be established by using the protooncogene of the present invention, and such a cell line may be obtained, for example, from tumor tissues formed on the back of a nude mouse by injecting fibroblast cells transformed with the protooncogene of the present invention. The cell lines thus prepared may be advantageously used in searching for anti-cancer agents.

The following Examples and Test Examples are given for the purpose of illustration only, and are not intended to limit the scope of the invention.

EXAMPLE 1

Differential Display of mRNA (Step 1) Isolation of Total RNA

Normal exocervical tissue specimens were obtained from uterine myoma patients during hysterectomy, and untreated primary cervical cancer and metastatic common iliac lymph node tissue specimens were obtained during radical hysterectomy. The human cervical cancer cell line CUMC-6 (Kim J W et al., *Gynecol Oncol*, 62: 230–240 (1996)) was cultured in Waymouth MB 751/1 medium.

Total RNAs were extracted from the tissue specimens and cells using a commercial system (RNeasy total RNA kit, Qiagen Inc., Germany), and DNA contaminants were removed therefrom using Message clean kit (GenHunter Corp., Brookline, Mass.).

(Step 2) Differential Display

Differential display was conducted according to Liang et al. (*Science*, 257: 967–971 (1992); and *Cancer Res.*, 52: 6966–6968 (1992)) with minor modifications as follows.

0.2 $\mu$g each of the total RNAs obtained in Step 1 was subjected to reverse transcription using primer of SEQ ID NO: 3, as an anchored oligo-dT primer (RNAimage kit, GenHunter), followed by polymerase chain reaction (PCR) using the same anchored primer and the arbitrary 5' 13 mer (RNAimage primer set 1, H-AP 1–32) in the presence of 0.5 mM [$\alpha$-$^{35}$S]-labeled dATP (1200 Ci/mmol). The PCR thermal cycle was repeated 40 times, each cycle being composed of: 95° C. for 40 sec., 40° C. for 2 min. and 72° C. for 40 sec., and finally the reaction was carried out at 72° C. for 5 min. The PCR product thus obtained was subjected to electrophoresis in 6% polyacrylamide sequencing gels, followed by autoradiography.

FIG. 1 shows the differential display results of normal exocervical tissue, cervical cancer tissue, metastatic tissue and cervical cancer cell line CUMC-6 using the anchored oligo-dT primer H-T11C(SEQ ID NO: 5) and the arbitrary 5' 13 mer of SEQ ID NO: 3 wherein the arrow indicates a 206 bp fragment, designated CC214, expressed in the cervical cancer and metastatic common iliac lymph node tissue, and human cervical cancer cell line CUMC-6.

The band of fragment CC214 was excised from the dried sequencing gel and boiled in water for 15 min. to elute fragment CC214. The fragment CC214 was subjected to PCR using the same conditions except that [α-$^{35}$S]-labeled DATP and 20 μM dNTPs were omitted. The amplified fragment CC214 was cloned into the pGEM-T Easy vector using the TA Cloning System (Promega, USA) and its nucleotide sequence was determined using the Sequenase Version 2.0 DNA Sequencing System (United States Biochemical Co., USA). Comparative analysis of the nucleotide sequence of fragment CC214 with GenBank database was conducted using BLAST and FASTA programs and the result showed that this fragment has little sequence similarity to any nucleotide sequence registered in the GenBank database.

EXAMPLE 2 cDNA Library Screening

A bacteriophage λgt11 human lung embryonic fibroblast cDNA library (generously provided by Prof. I Y Chung at Hanyang University, Seoul, Korea) was screened by plaque hybridization with $^{32}$P-labeled random-primed CC214 cDNA probe (Sambrook, J. et la., Molecular Cloning: A laboratory manual, New York: Cold Spring Harbor Laboratory (1989)) to obtain a full-length cDNA clone (designated HCCR-2). The nucleotide sequence of the full-length HCCR-2 cDNA clone was determined.

The full-length HCCR-2 cDNA clone contains a 2003 bp insert having the nucleotide sequence of SEQ ID NO: 1 and a full open reading frame corresponding to base Nos. 63 to 977 is a protein encoding region and the predicted amino acid sequence derived therefrom is shown in SEQ ID NO: 2 which consists of 304 amino acids. Further, the region represented by nucleotide No. 321 to 380 of SEQ ID NO: 1 encodes a single transmembrane domain having the predicted amino acid sequence of amino acid Nos. 87 to 106 of SEQ ID NO: 2. This suggests that the protooncogene of the present invention is a membrane-bound gene.

A single potential N-glycosylation site(corresponding to base Nos. 831 to 839 of SEQ ID NO: 1 and amino acid Nos. 257 to 259 of SEQ ID NO: 2) is present at the C-terminal side of the HCCR-2 protein, which suggests that HCCR-2 is a type II membrane protein. The polyadenylation signal corresponds to the nucleotide Nos. 1894–1898 of SEQ ID NO:1.

The nucleotide sequence of full-length HCCR-2 cDNA clone was registered at GenBank as accession no. AF315598.

The full-length HCCR-2 cDNA was inserted in vector pCEV-LAC (Miki, T. et al., Gene, 83: 137–146 (1989)) to obtain the recombinant vector HCCR-2/pCEV-LAC and E. coli JM109 was transformed with the recombinant vector HCCR-2/pCEV-LAC to obtain the transformed E. coli designated JM109/HCCR2 which was deposited with Korean Collection for Type Cultures (Address: #52, Oun-dong, Yusong-ku, Taejon 305–333, Republic of Korea) on Oct. 11, 1999 under the accession number of KCTC 0668BP.

EXAMPLE 3

Northern Blot Analysis

To determine the expression level of HCCR-2 gene in various normal tissues, cancer tissues and cancer cell lines, the northern blot analysis was conducted as follows.

Total RNAs were prepared from normal exocervical tissue, primary cervical cancer tissue; and human cervical cancer cell lines CaSki (ATCC CRL 1550) and CUMC-6 by repeating the procedure of Step 1 of Example 1. 20 μg each of the total RNAs were denatured and then electrophoresed through 1% formaldehyde agarose gel and transferred to nylon membranes (Boehringer-Mannheim, Germany). The blots were hybridized overnight at 42° C. with $^{32}$P-labeled random-primed HCCR-2 cDNA probe which was prepared using a rediprime II random prime labeling system (Amersham, England). The northern blot analysis results were consistently repeated two times, as quantified by densitometry and the same blots were hybridized with a β-actin probe to confirm mRNA integrity.

Using normal human 12 multiple-tissues (Clontech) and human cancer cell lines (Clontech), northern blot analyses were also carried out as recommended by the supplier.

Figure 2:
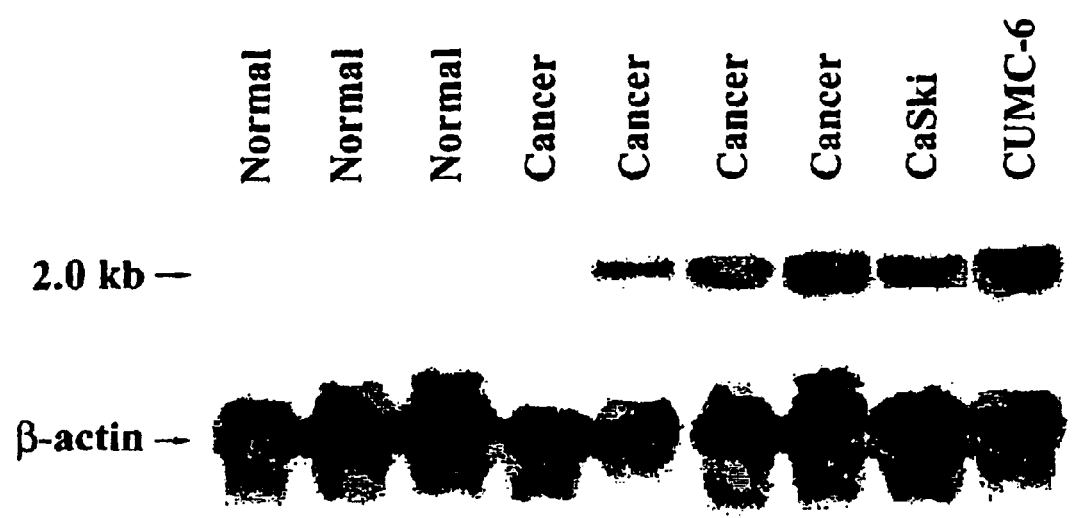
FIG. 2: the results of northern blot analyses for HCCR-2 gene expressed in normal cervical tissues, cervical cancer tissues and cervical cancer cell lines(CaSki and CUMC-6)

FIG. 2 shows the northern blot analysis results of normal cervical tissues, primary cervical cancer tissues and cervical cancer cell lines CUMC-6 and CaSki using the HCCS-1 cDNA probe; and the same blot hybridized with a β-actin probe. As can be seen from FIG. 2, the expression level of HCCR-2 gene was elevated in the cervical cancer tissues and the cervical cancer cell lines but nearly absent in all normal cervical tissues.

Figure 3A:
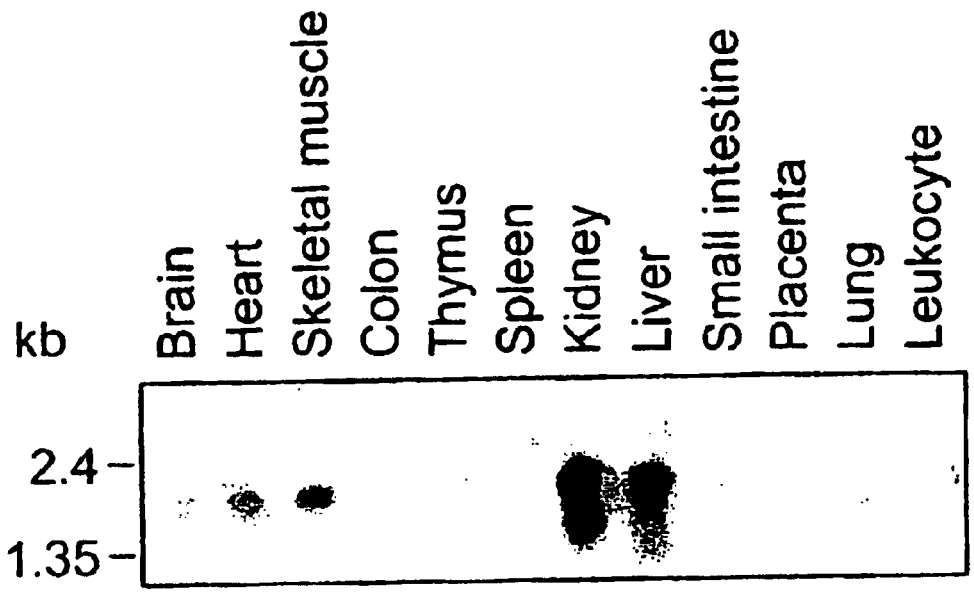
FIG. 3A: the results of northern blot analyses for HCCR-2 gene expressed in normal human 12-lane multiple tissues.
Figure 3B:
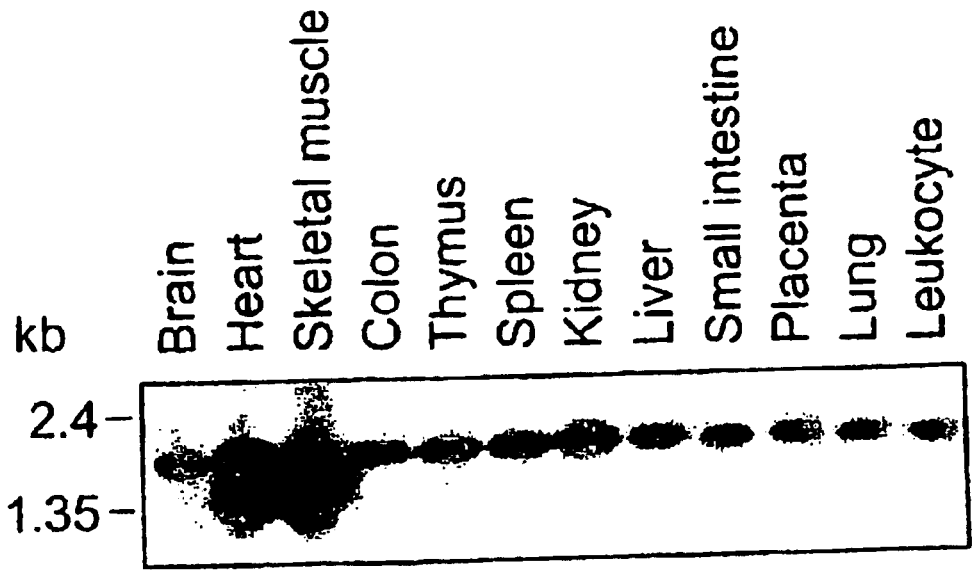
FIG. 3B: the results obtained with the same sample of FIG. 3A hybridized with β-actin.

FIG. 3A shows the northern blot analysis results of normal human tissues, i.e., brain, heart, skeletal muscle, colon, thymus, spleen, kidney, liver, small intestine, placenta, lung and peripheral blood leukocyte using HCCR-2 cDNA probe; and FIG. 3B, the same blot hybridized with a β-actin probe. As can be seen in FIG. 3A, HCCR-2 mRNA (~2.0 kb) is weakly present or absent in many normal tissues, but the level of expression was high in normal kidney tissue.

Figure 4A:
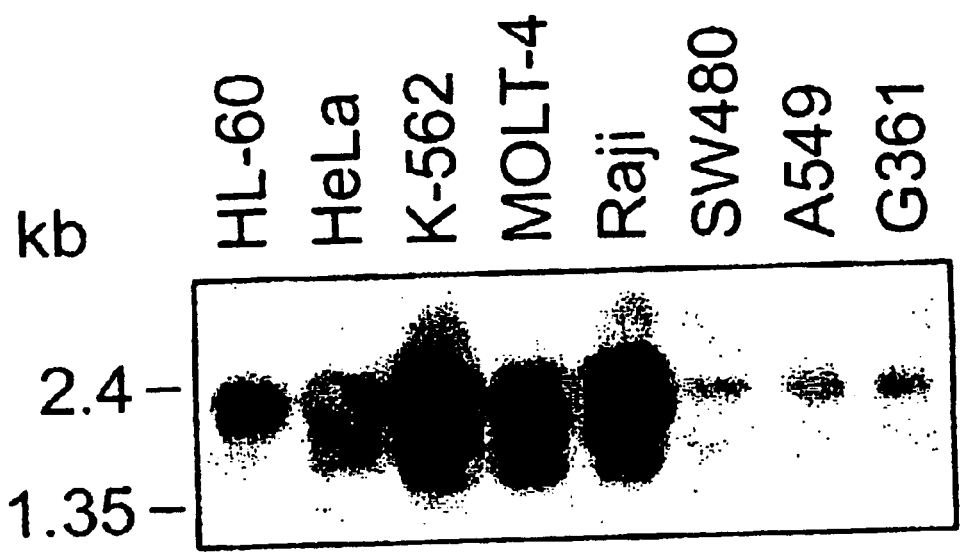
FIG. 4A: the results of northern blot analyses for HCCR-2 gene expressed in human cancer cell lines.
Figure 4B:
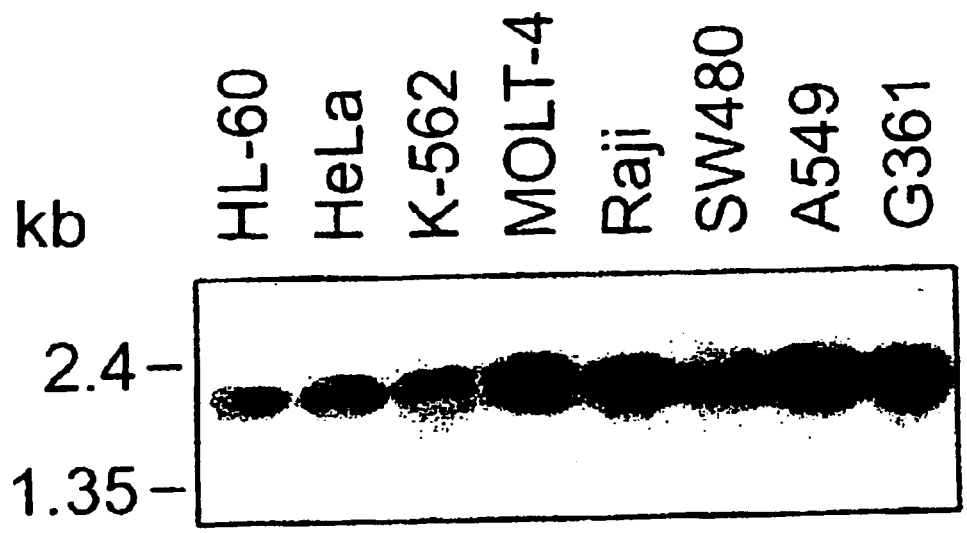
FIG. 4B: the results obtained with the same sample of FIG. 4A hybridized with β-actin.

FIG. 4A shows the northern blot analysis for HCCR-2 gene expressed in results of human leukemia and lymphoma cell lines, i.e., promyelocytic leukemia HL-60 cell, HeLa cervical cancer cell, chronic myelogenous leukemia K-562 cell, lymphoblastic leukemia MOLT-4 cell, Burkitt's lymphoma Raji cell, SW480 colon cancer cell, A549 lung cancer cell and G361 melanoma cell using the HCCR-2 cDNA probe; and FIG. 4B, the same blot hybridized with a β-actin probe. As can be seen in FIGS. 4A and 4B, HCCR-2 is transcribed at a high level in the human leukaemia and lymphoma cell lines such as chronic myelogenous leukaemia K-562, Burkitt's lymphoma Raji, lymphoblastic leukaemia MOLT-4 and promyelocytic leukaemia HL-60 as well as HeLa cells.

K-562, MOLT-4 and HL-60, in particular, show higher transcription levels as compared with normal leukocyte by factors of approximately 190, 90 and 70, respectively. HCCR-2 expression levels in colorectal cancer SW480, lung cancer A549 and melanoma G361 cell lines are lower than those of leukemia and lymphoma.

Figure 5A:
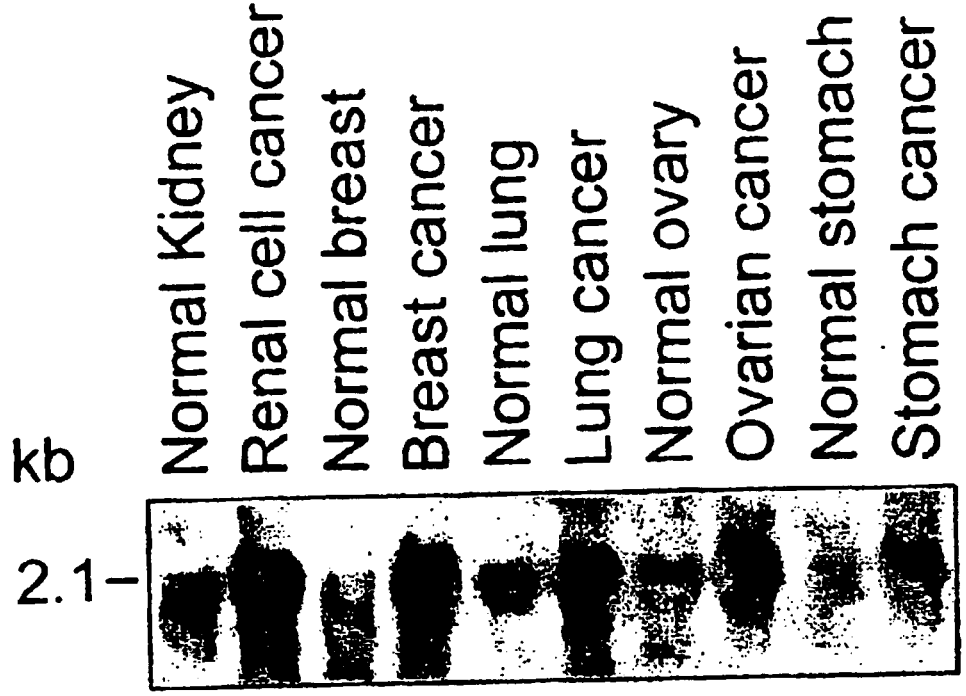
FIG. 5A: the results of northern blot analyses for HCCR-2 gene expressed in human tumor tissues and their normal counterparts.
Figure 5B:
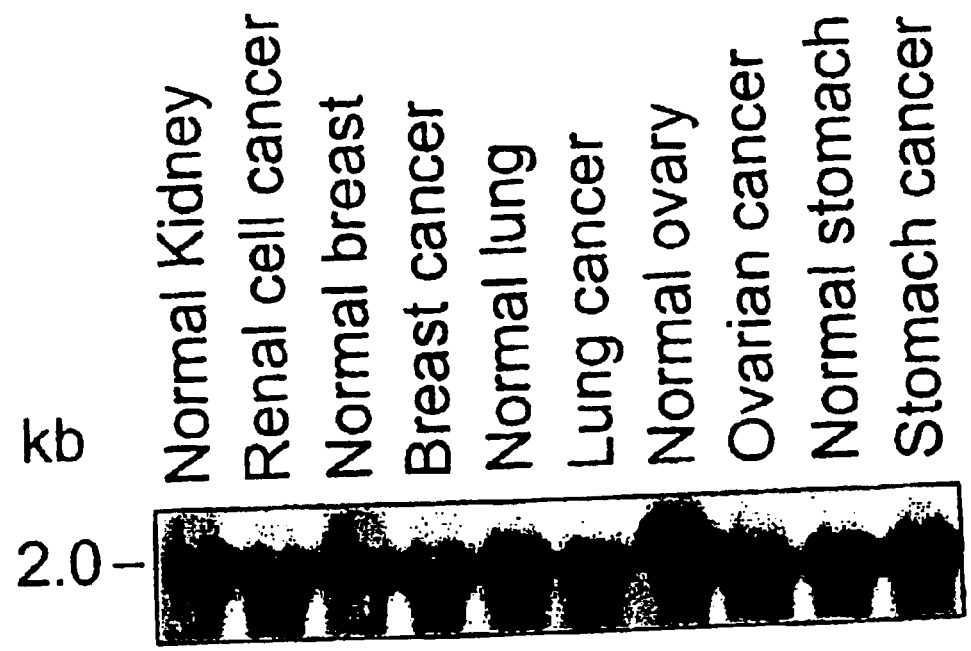
FIG. 5B: the results obtained with the same sample of FIG. 5A hybridized with β-actin.

Further, northern blotting analyses of the human kidney, breast, lung, ovary and stomach cancer tissues and their normal counterparts were carried out. As shown in FIG. 5A, HCCR-2 was transcribed at a high level in the human cancer cells, while the expression of HCCR-2 gene is barely observable in the normal cells. FIG. 5B shows the results obtained with the same samples hybridized with β-actin probe to confirm mRNA ingegrity.

EXAMPLE 4

Construction of Expression Vectors and Transformation of Animal Cells (Step 1) Preparation of a Vector Containing HCCR-2

An expression vector containing the coding region of HCCR-2 was constructed as follows.

First, the entire HCCR-2 cDNA obtained in Example 2 was inserted into the SalI restriction site of a prokaryotic expression vector, pCEV-LAC(see Miki, T. et al., *Gene*, 83: 137–146 (1989)). Then, the SalI fragment was isolated from the pCEV-LAC/HCCR-2 vector.

Then, pcDNA3 (Invitrogen) was digested with XhoI to make a compatible end with SalI. The SalI fragment containing the full length HCCR-2 coding sequence was inserted into the XhoI-digested pcDNA3. Lipofectamine (Gibco BRL) was used to introduce the resulting pcDNA3/HCCR-2 expression vector into NIH/3T3 cells(ACTC CRL, 1658, USA), followed by selection in a medium supplemented with G418 (Gibco). The resulting NIH/3T3 cells transfected with HCCR-2 was designated "HCCR-2M cells". Another population of NIH/3T3 cells containing pcDNA3 alone was prepared as a control and designated "pcDNA3 cells".

(Step 2) NIH13T3 Fibroblast Cells Transfected with the HCCR-2 Protooncogene

Figure 6:
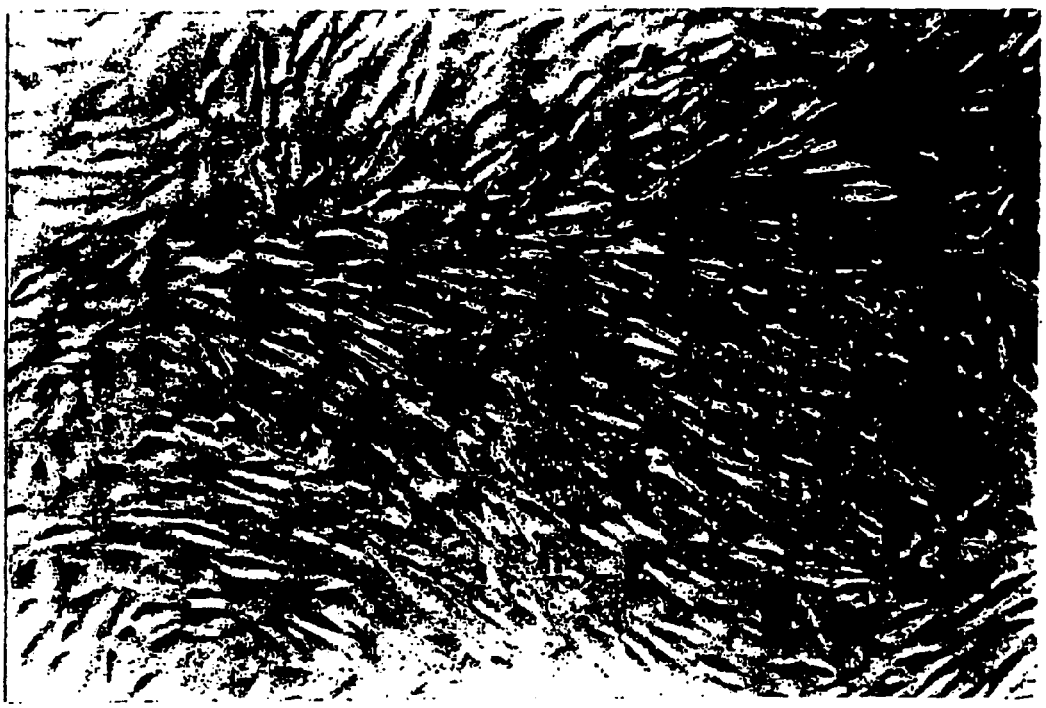
FIG. 6: a phase-contrast feature of monolayer-cultured wild type NIH/3T3 cells.
Figure 7:
FIG. 7: a phase-contrast feature of monolayer-cultured HCCR-2-transfected NIH/3T3 cells (HCCR-2M cells)

The wild type normal NIH/3T3 cell, a differentiated fibroblast cell line, is a spindle shaped cell having a long slender nucleus and a scanty amount of cytoplasm as shown in FIG. 6. When HCCR-2 was expressed in the NIH/3T3 expressing HCCR-2 (HCCR-2M cells) obtained in Step 1, the cell shape changes into a polygonal form with an ovoid nucleus and plump cytoplasm, as shown in FIG. 7.

Figure 8:
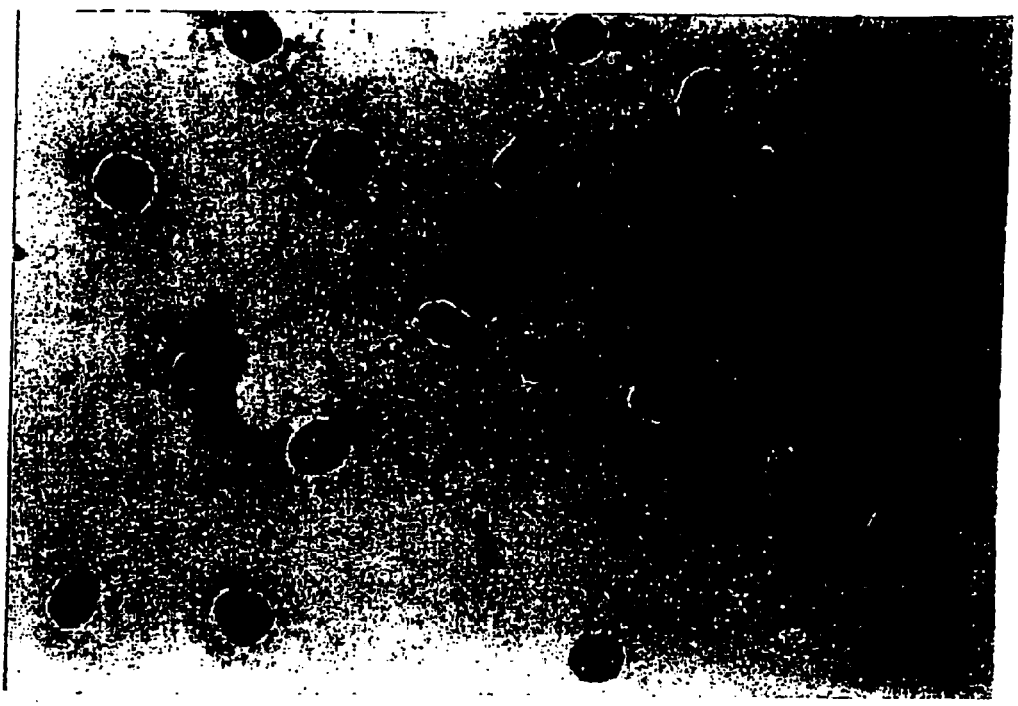
FIG. 8: hematoxylin-eosin staining of monolayer-cultured HCCR-2-transfected NIH/3T3 cells.

Monolayer cultured HCCR-2-transfected NIH/3T3 cells which is stained with hematoxylin-eosin, exhibit nuclear pleiomorphism, distinct nucleoli, granular chromatin patterns, tumor giant cells and atypical mitotic figures as shown in FIG. 8.

EXAMPLE 5

Tumorigenicity of HCCR-2M Cell in Animal

To analyze tumourigenicity, $5 \times 10^6$ HCCR-2-transfected NIH/3T3 cells(HCCR-2M cells) were injected subcutaneously into the posterior lateral aspect of the trunk of 10 mice (5-week-old athymic nu/nu on BALB/c background). Nude mice were sacrificed when the subcutaneous tumors reached 1.5–2.5 cm in diameter.

Figure 9:
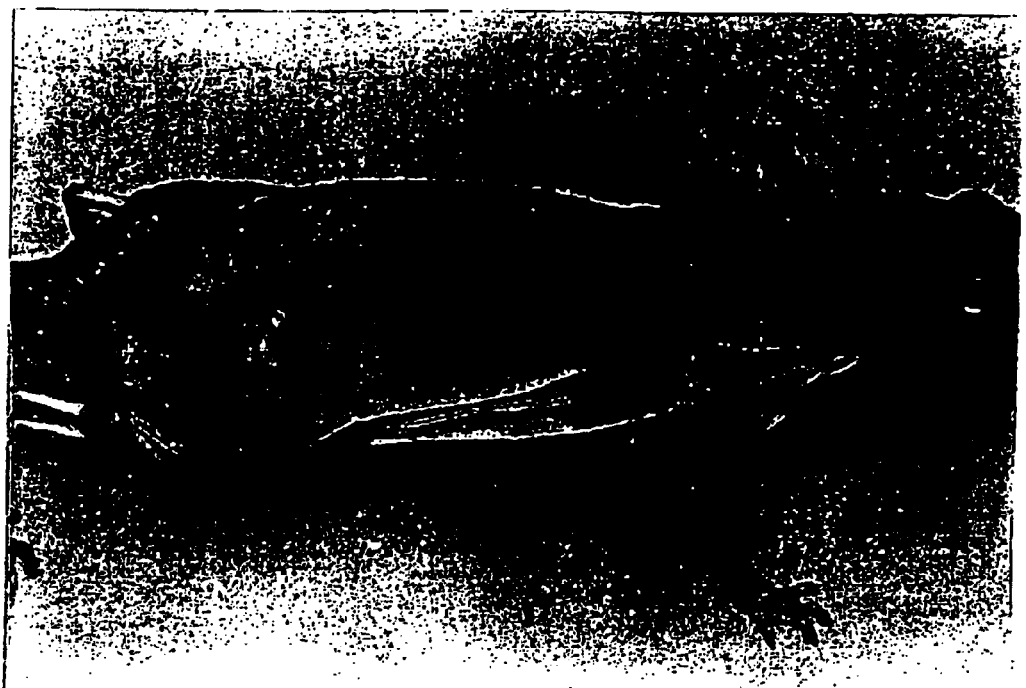
FIG. 9: tumorigenicity of HCCR-2-transfected NIH/3T3 cells in nude mouse.

All 10 mice injected with HCCR-2M cells showed palpable tumors after 21 days as shown in FIG. 9.

Figure 10:
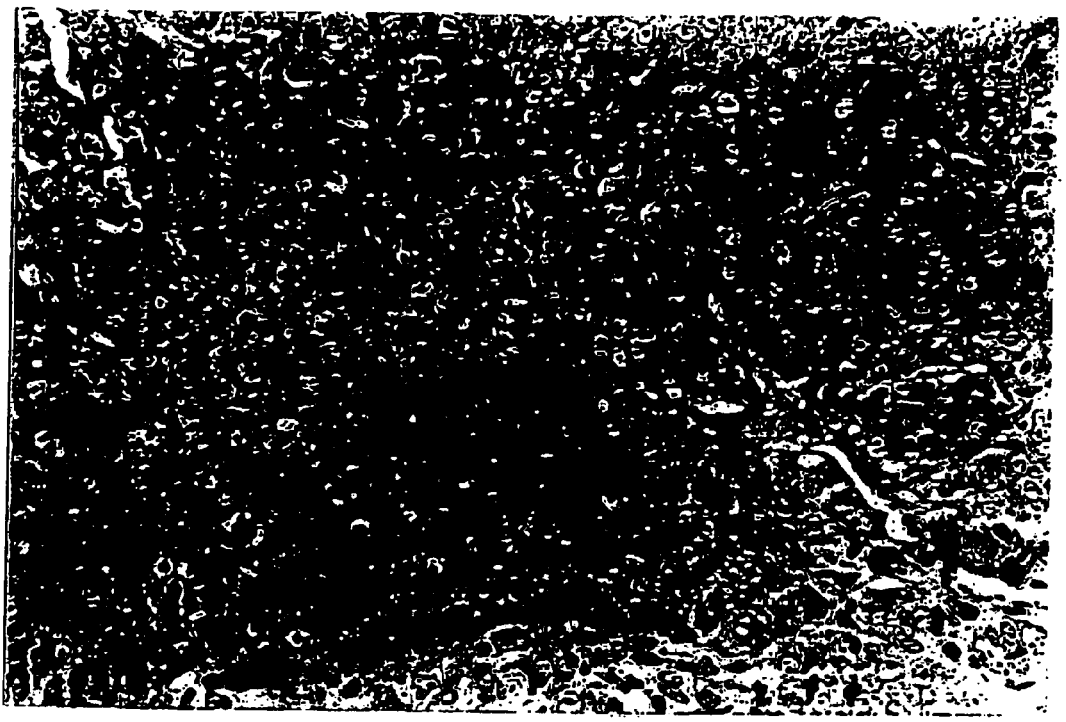
FIG. 10: hematoxylin-eosin staining of subcutaneous tumor nodules derived from HCCR-2-transfected NIH/3T3 cells in nude mice.

Nude mice bearing HCCR-2M allografts display characteristics of an epithelial carcinoma. FIG. 10 shows hematoxylin-eosin staining of subcutaneous tumor nodules taken from the nude mice. The sections of the tumor nodules revealed typical epithelial cell nests separated by fibrous stroma.

EXAMPLE 6

Figure 11:
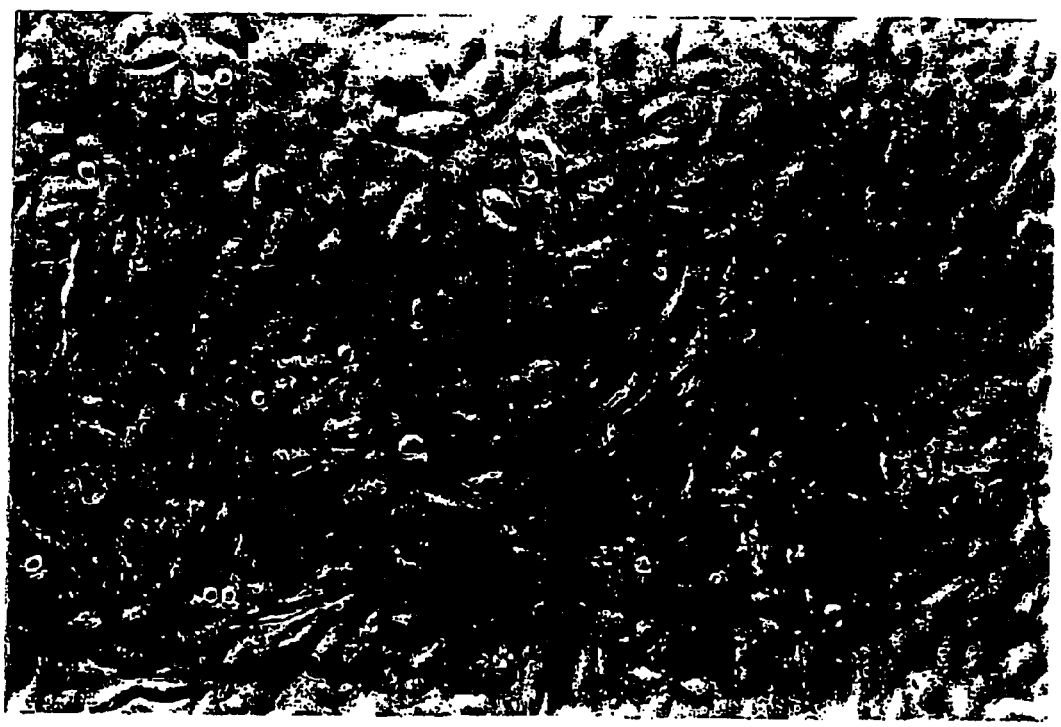
FIG. 11: phase-contrast features of monolayer-cultured nude mice-derived HCCR-2MN cells.

Establishment of New Cancer Cell Line from HCCR-2M Cell-Induced Tumor Tissue The cells obtained from the tumor tissue of Example 5 was cultured in a conventional manner using 20% fetal bovine serum and the cultured cells were designated HCCR-2MN cells which have cytological features similar to HCCR-2M cells in vitro as shown in FIG. 11.

EXAMPLE 7

Determination of Size of Protein Expressed after the Transfection of *E. coli* with HCCR-2 Protooncogene A full-length HCCR-2 protooncogene of SEQ ID NO: 1 was inserted into the multiple cloning site of pET-32b(+) vector(Novagen) and the resulting pET-32b(+)/HCCR-2 vector was transfected into *E. coli* BL21(ATCC 47092). The transfected *E. coli* was incubated using an LB broth medium in a rotary shaking incubator, diluted by $\frac{1}{100}$, and incubated for 3 hours. 1 mM isopropyl β-D-thiogalacto-pyranoside (IPTG, Sigma) was added thereto to induce the protein synthesis.

Figure 12:
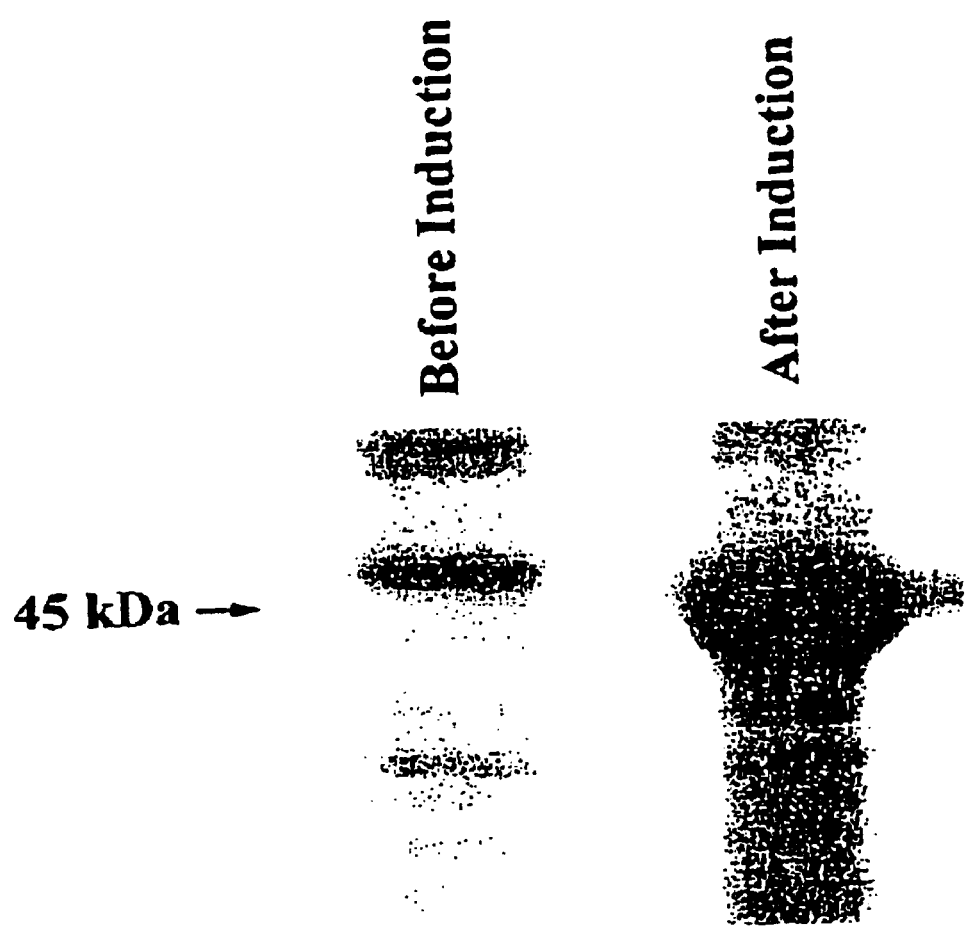
FIG. 12 sodium dodecyl sulfate (SDS)-PAGE results showing protein expression patterns before and after the IPTG induction.

The *E. coli* cells in the culture were disrupted by sonication and subjected to gel electrophoresis using 12% sodium dodecyl sulfate(SDS) before and after the IPTG induction. FIG. 12 shows the SDS-PAGE results which exhibit a protein expression pattern of the *E. coli* BL21 strain transfected with pET-32b(+)/HCCR-2 vector. After the IPTG induction, a significant protein band was observed at about 45 kDa. This 45 kDa fused protein contained an about 20 kDa Trix-Tag thioredoxin protein expressed a the gene in pET-32b(+) vector.

EXAMPLE 8

Production of Antibody

The 45 kDa fused protein isolated from the *E. coli* BL21 strain transfected with pET-32b(+)/HCCR-2 vector in Example 7 was purified by using a His-Bind Kit (Novagen). Immunoblotting of the purified peptide confirmed the presence of a major amount of a 45 kDa protein.

Then, two 6-seek old Sprague-Dawley rats each weighing about 150 g were each subcutaneously immunized with 1 mg of the peptide thus obtained, weekly for 3 times. Blood samples were obtained from the immunized rats and centrifuged to obtain a polyclonal serum. The anti-HCCR-2 activity of the polyclonal serum was determined and confirmed by enzyme-linked immunosorbent assay(1:10,000)

EXAMPLE 9

Immunoblot Confirming Antibody Specificity

For western blot analysis, the cell identified in FIG. 7 was harvested and lysed in a Laemmli sample buffer in accordance with the method described by Laemmli (*Nature*, 227: 680–685(1970)). The cellular protein was separated by 10% SDS-PAGE and then electroblotted onto nitrocellulose membranes. The membranes were incubated with the rat polyclonal anti-HCCR-2 serum prepared in Example 8 for 16 h. After washing, the membranes were incubated with a blocking solution containing 1:1,000 dilution of peroxidase-conjugated goat anti-rat immunoglobulin (Jackson ImmunoResearch) as a secondary antibody. Proteins were revealed by an ECL-Western blot detection kit (Amersham).

Figure 13:
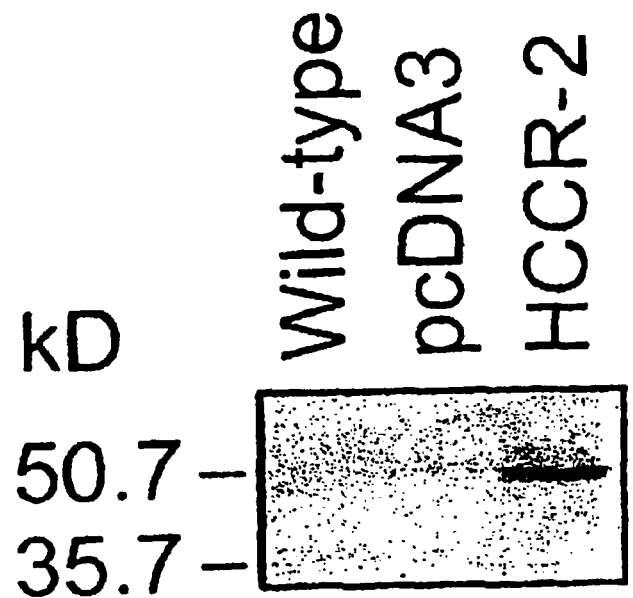
FIG. 13: the result of western blotting analysis of NIH/3T3 cells without transfection(wild type), NIH/3T3 transfected with pcDNA3 vector alone(pcDNA3) and HCCR-2-transfected NIH/3T3 cells (HCCR-2M cells)

As shown in FIG. 13, HCCR-2 protein is overexpressed in HCCR-2 cells, while only faint bands are observed for the wild type and cells transfected with the vector alone (pcDNA3). This result illustrates the specificity of the anti-HCCR-2 antibodies in the polyclonal serum.

Figure 14:
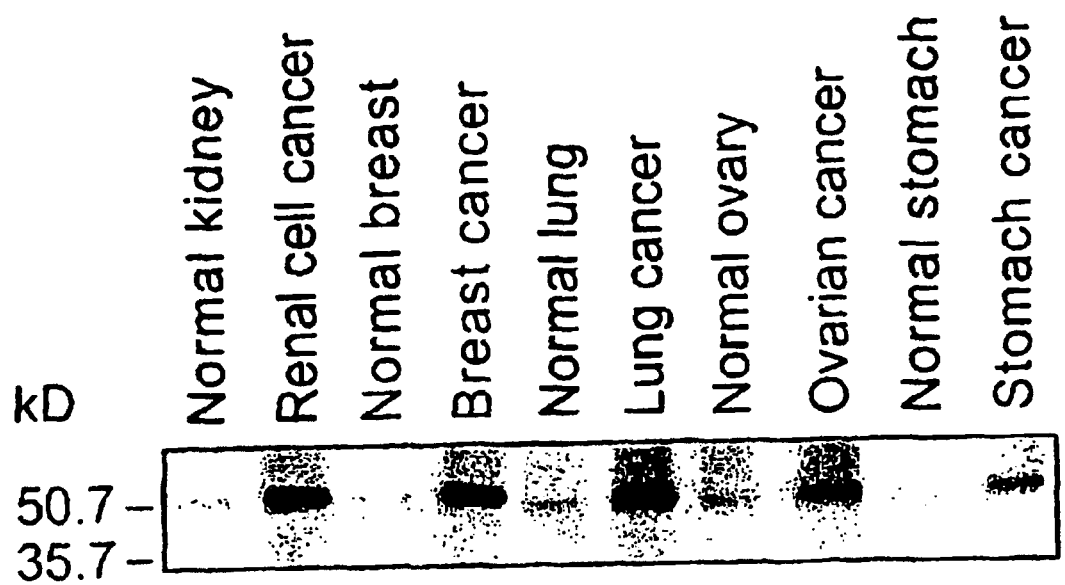
FIG. 14: the result of western blotting analysis of human tumor tissues of kidney, breast, lung, ovary and stomach and their normal counterparts.

Further, the HCCR-2 antibody in the polyclonal serum recognized approximately 45 kDa protein in human protein extracts from different tissues. As shown in FIG. 14, human tumor tissues including carcinomas of the kidney, breast, lung, ovary and stomach showed increased HCCR-2 protein expression when compared with their normal counterparts.

EXAMPLE 10

Immunohistochemical Staining

To determine the expression level of HCCR-2 protein in various normal tissues and cancer tissues, the immunohistochemical stainings were conducted according to the avidin-biotin-peroxidase complex method (Hsu, S. M. et al., *Histochem Cytochem*, 29: 577–580 (1981)) as follows.

The paraffin-embedded tissues were dewaxed using xylene, treated with graded ethanol, rehydrated after removing paraffin and washed with water. Then, the tissues were placed in peroxide quenching solution made with hydrogen peroxide for 30 minutes to remove the endogenous peroxidase activity, treated with serum blocking solution (Zymed Laboratories, CA, USA) for 30 minutes to block non-specific binding, treated with the primary antibody, left for overnight at 4° C., washed with phosphate-buffered saline (PBS), treated with the biotinylated secondary antibody (Zymed) for 30 minutes, and washed with PBS. Then, the tissues were treated with an enzyme conjugate for 30 minutes, washed with PBS, treated with the aminoethyl carbazole (Zymed) as a chromogen for 18 minutes. Then, the tissue sections were counterstained with hematoxylin.

Figure 15A:
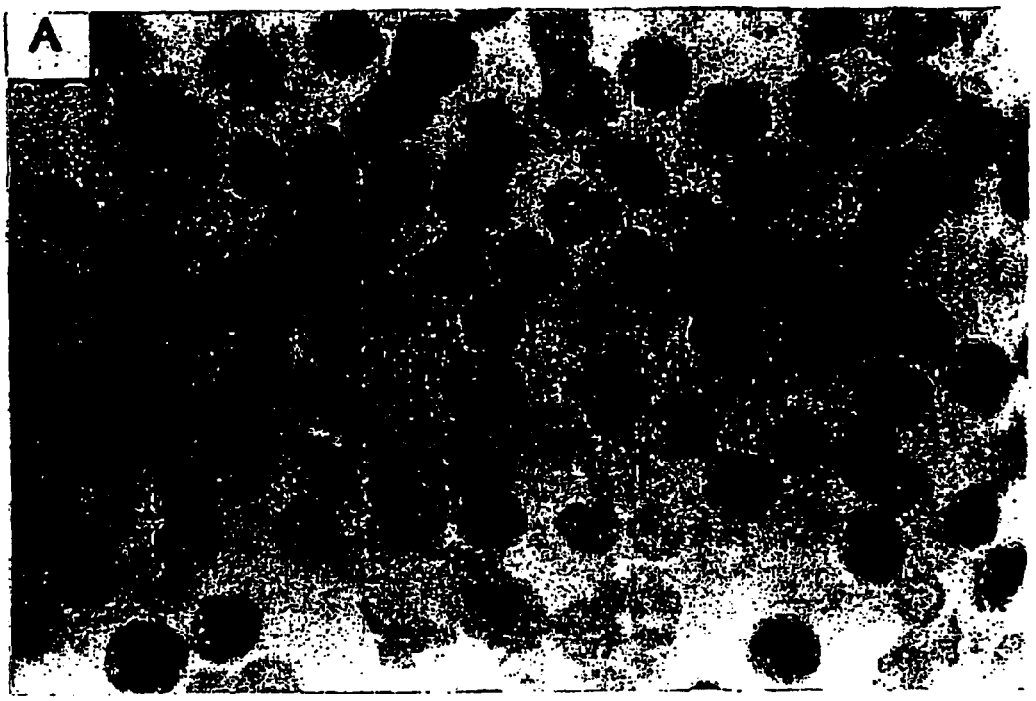
FIGS. 15A and 15B: the results of immunohistochemical stainings for HCCR-2 protein expressed in normal leukocytes and human leukemia cells (×200)
Figure 15B:
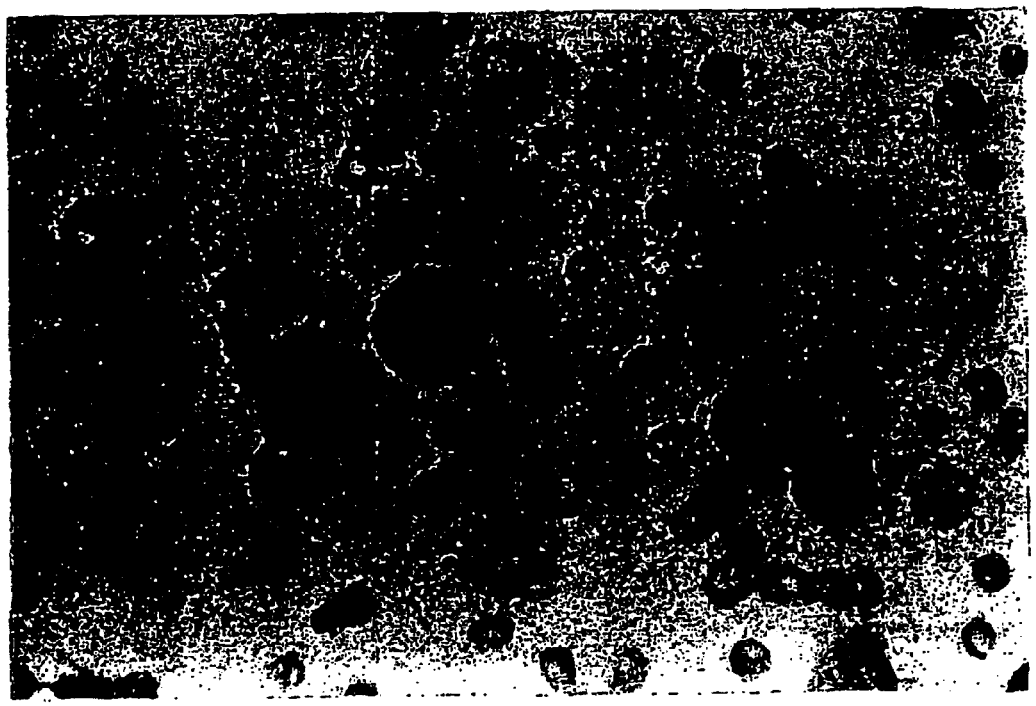

FIG. 15 shows the immunohistochemical staining results of normal leukocytes(A) and leukemic cells(B). The normal leukocytes show negative intensity of expression and leukemic cells show strong positive intensity of expression.

Figure 16A:
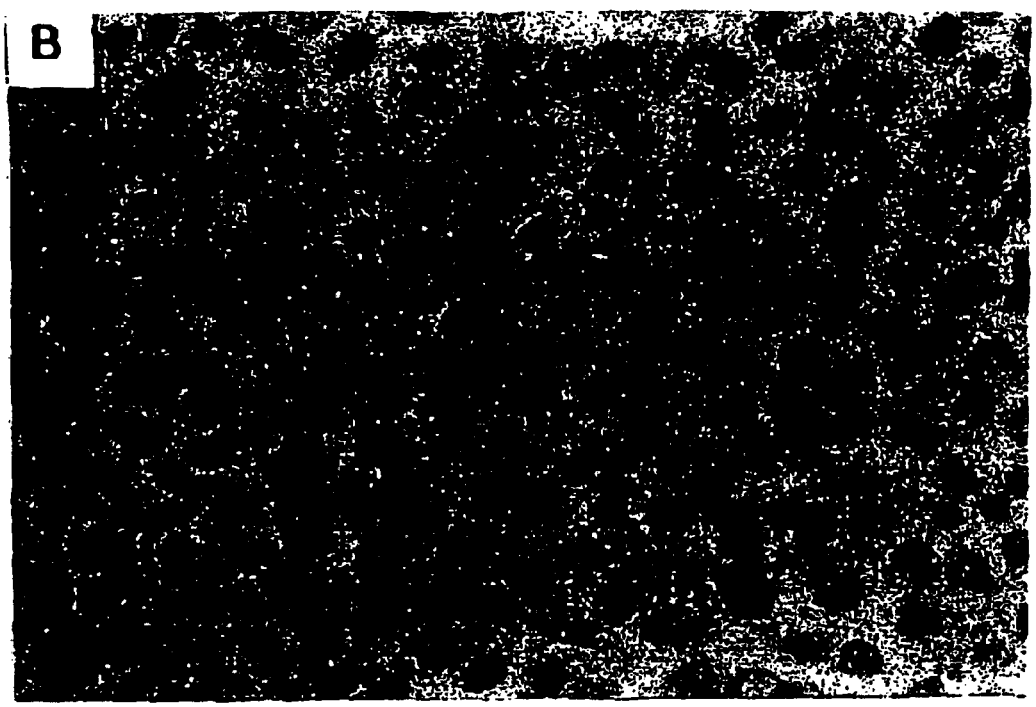
FIGS. 16A and 16B: the results of immunohistochemical stainings for HCCR-2 protein expressed in normal lymphocytes and human lymphoma tissue (×200)
Figure 16B:

FIG. 16 shows the immunohistochemical staining results of normal lymphocyte(A) and lymphoma tissue(B). The normal lymphocytes show negative intensity of expression and lymphoma tissue shows strong positive intensity of expression in the cytoplasm.

Figure 17A:
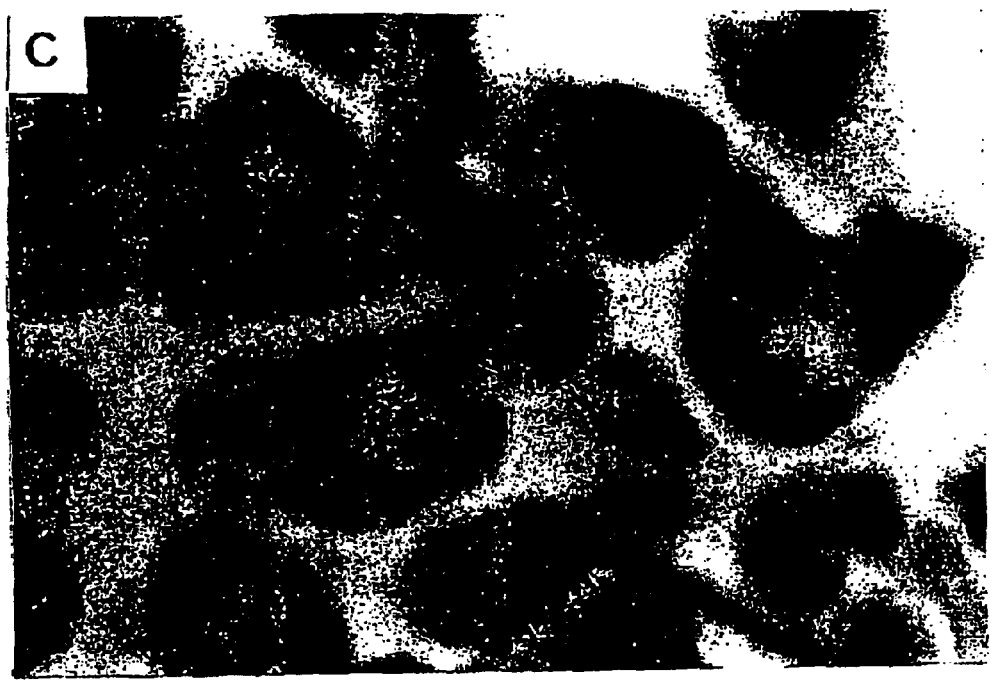
FIGS. 17A and 17B: the results of immunohistochemical stainings for HCCR-2 protein expressed in normal breast tissue and human breast cancer (×200)
Figure 17B:
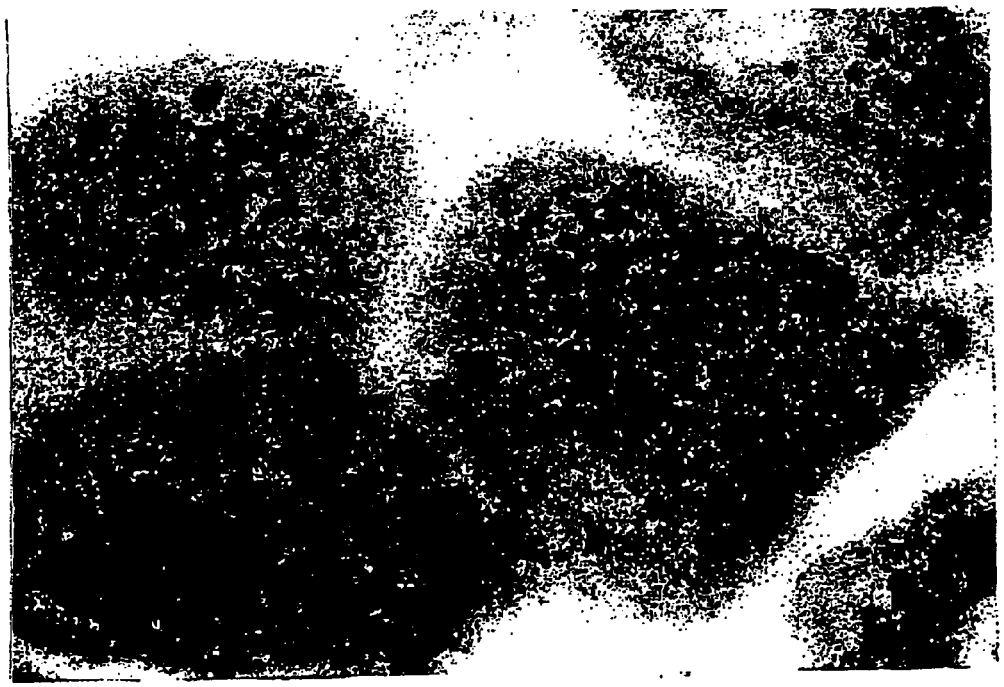

FIG. 17 shows the immunohistochemical staining results of normal breast tissue(A) and breast tumor tissue(B). The normal breast tissue shows negative intensity of expression and breast tumor tissue shows strong positive intensity of expression in the cytoplasm.

Figure 18A:
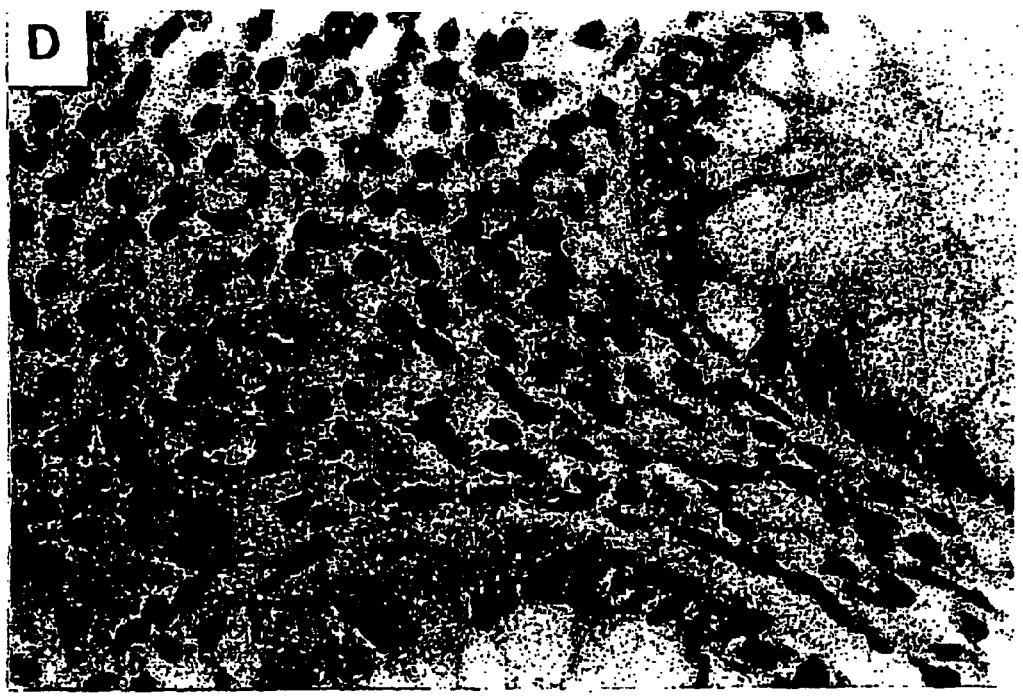
FIGS. 18A and 18B: the results of immunohistochemical stainings for HCCR-2 protein expressed in normal colon tissue and human colon cancer (×100)
Figure 18B:

FIG. 18 shows the immunohistochemical staining results of normal colon tissue(A) and colon cancer tissue(B). The normal colon tissue shows negative intensity of expression and colon cancer tissue shows strong positive intensity of expression in the cytoplasm.

Figure 19A:
FIGS. 19A and 19B: the results of immunohistochemical stainings for HCCR-2 protein expressed in normal kidney tissue and human kidney tumor tissue (×100)
Figure 19B:

FIG. 19 shows the immunohistochemical staining results of normal kidney tissue(A) and renal cancer tissue(B). The normal kidney tissue shows negative intensity of expression and kidney tumor tissue shows strong positive intensity of expression in the cytoplasm.

Figure 20A:
FIGS. 20A and 20B: the results of immunohistochemical stainings for HCCR-2 protein expressed in normal cervical tissue and human cervical cancer tissue (×100)
Figure 20B:
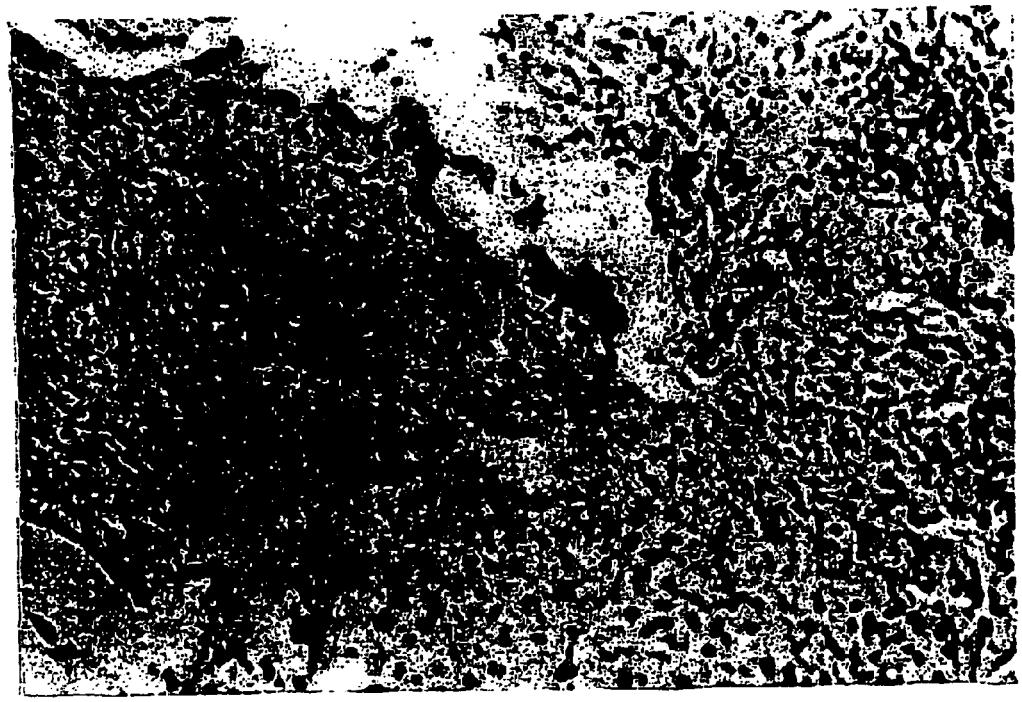

FIG. 20 shows the immunohistochemical staining results of normal cervical tissue(A) and cervical cancer tissue(B). The portion of normal cervical tissue shows negative intensity of expression and cervical cancer tissue shows strong positive intensity of expression.

EXAMPLE 11

Construction of Expression Vectors and Transformation of Human Cells (Step 1) Preparation of a Vector Containing HCCR-2

An expression vector containing the coding region of HCCR-2 was constructed as follows.

First, the entire HCCR-2 cDNA obtained in Example 2 was inserted into the SalI restriction site of a prokaryotic expression vector, pCEV-LAC(see Miki, T. et al., *Gene*, 83: 137–146 (1989)). Then, the SalI fragment was isolated from the pCEV-LAC/HCCR-2 vector.

Then, pcDNA3 (Invitrogen) was digested with XhoI to make a compatible end with SalI. The SalI fragment containing the full length HCCR-2 coding sequence was inserted into the XhoI-digested pcDNA3. Lipofectamine (Gibco BRL) was used to introduce the resulting pcDNA3/HCCR-2 expression vector into human embryonic kidney 293 epithelial cells(ACTC CRL, 1573, USA), followed by selection in a medium supplemented with G418 (Gibco). The resulting 293 epithelial cells transfected with HCCR-2 was designated "HCCR-2H cells".

(Step 2) 293 Epithelial Cells Transfected with the HCCR-2 Protooncogene

Figure 21:
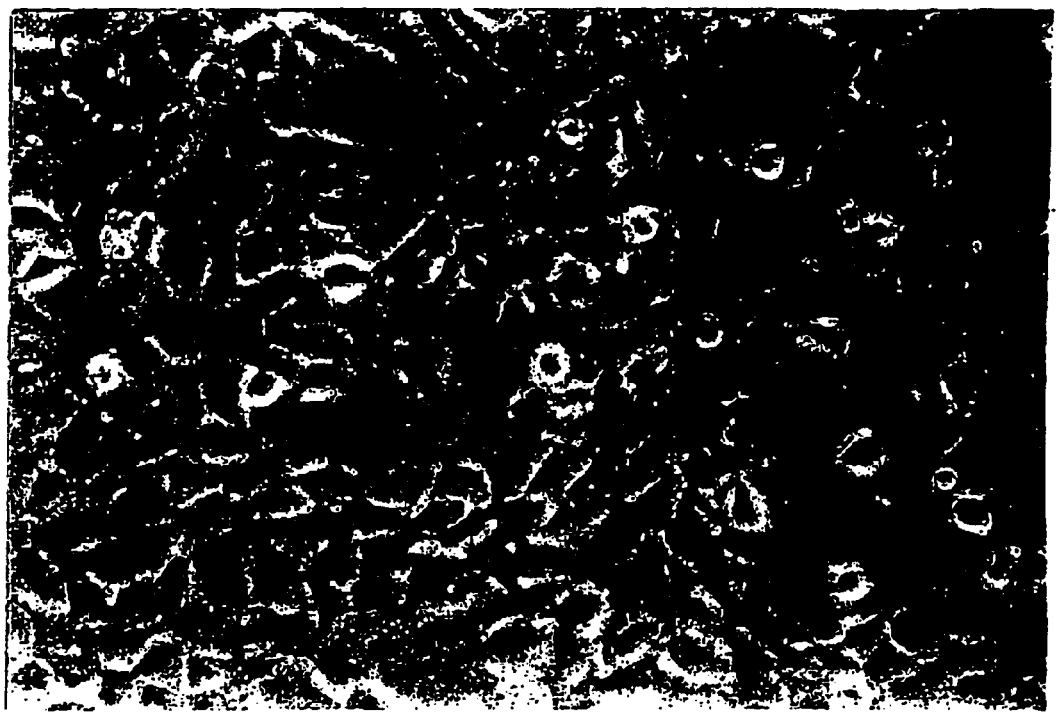
FIG. 21: phase-contrast features of monolayer-cultured wild type human embryonic kidney 293 epithelial cells.
Figure 22:
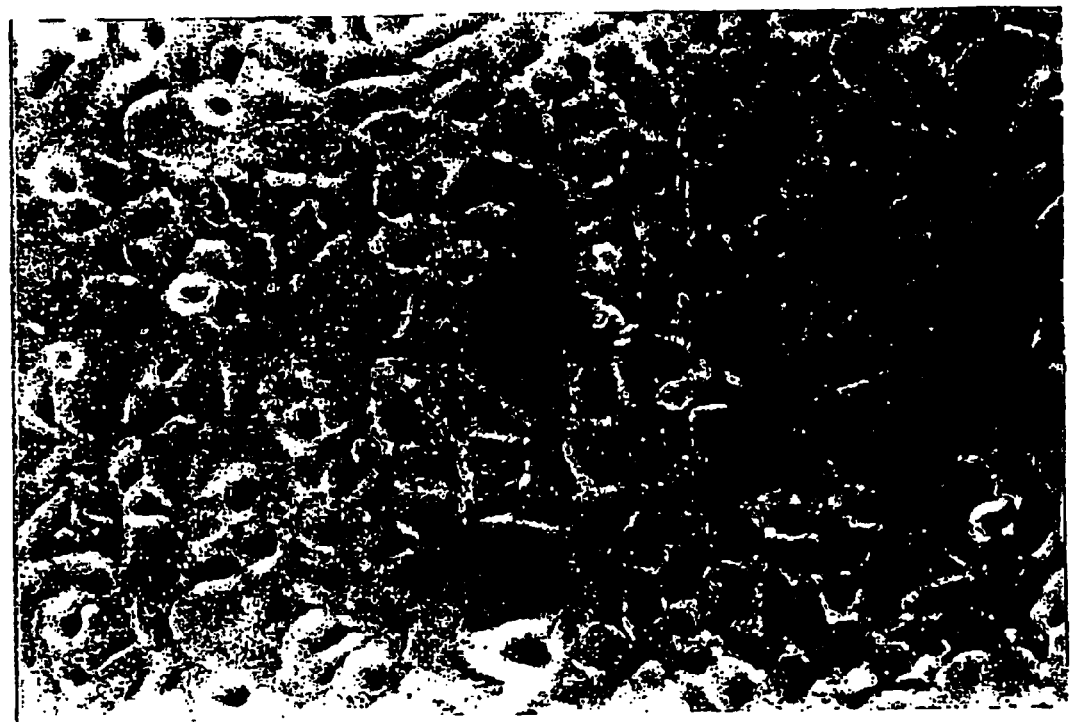
FIG. 22: phase-contrast features of monolayer-cultured HCCR-2-transfected 293 epithelial cells (HCCR-2H cells)

The wild type human embryonic kidney 293 epithelial cell, a differentiated fibroblast cell line, is a spindle shaped cell having a long slender nucleus and a scanty amount of cytoplasm as shown in FIG. 21. When HCCR-2 was expressed in the 293 epithelial cell expressing HCCR-2 (HCCR-2H cells) obtained in Step 1, the cell shape changes into a polygonal form with an ovoid nucleus and plump cytoplasm, as shown in FIG. 22.

Figure 23:
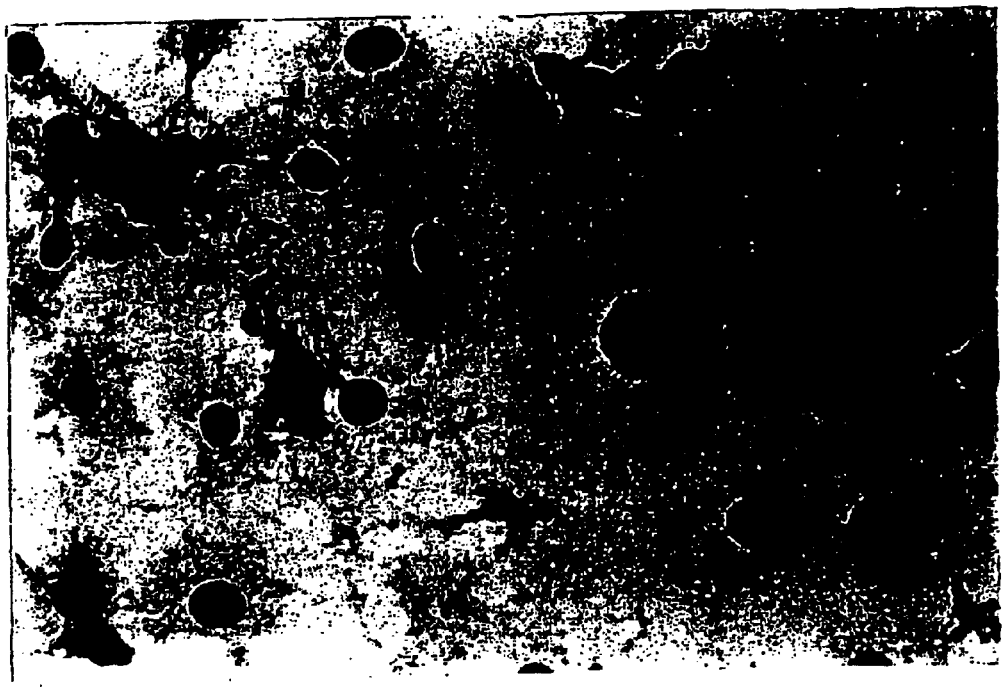
FIG. 23: hematoxylin-eosin staining of monolayer-cultured HCCR-2-transfected 293 epithelial cells.

Monolayer cultured HCCR-2-transfected 293 epithelial cells which are stained with hematoxylin-eosin, exhibit nuclear pleiomorphism, distinct nucleoli, granular chromatin patterns, tumor giant cells and atypical mitotic figures as shown in FIG. 23.

EXAMPLE 12

Tumorigenicity of HCCR-2H Protooncogene in Animal

To analyze tumourigenicity, $5 \times 10^6$ HCCR-2-transfected human embryonic kidney 293 epithelial cells(HCCR-2H cells) were injected subcutaneously into the posterior lateral aspect of the trunk of 10 mice (5-week-old athymic nu/nu on BALB/c background). Nude mice were sacrificed when the subcutaneous tumors reached 1.5–2.5 cm in diameter.

Figure 24:
FIG. 24: tumorigenicity of HCCR-2-transfected 293 epithelial cells in nude mouse.

All 10 mice injected with HCCR-2H cells showed palpable tumors after 20 days as shown in FIG. 24.

Figure 25:
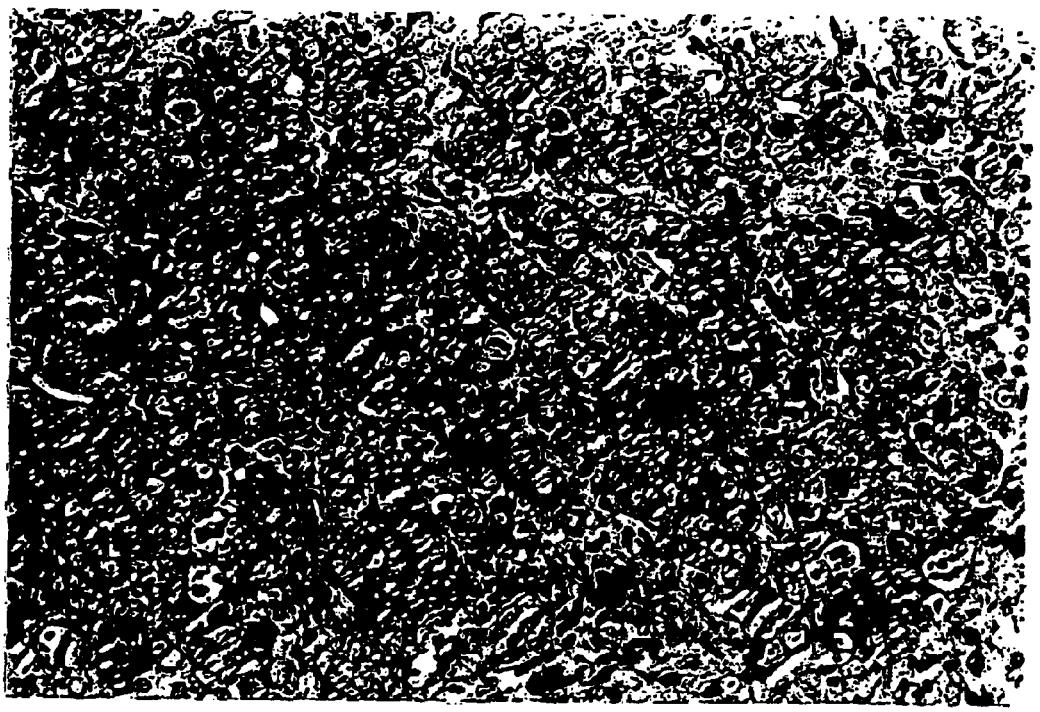
FIG. 25: hematoxylin-eosin staining of subcutaneous tumor nodules derived from HCCR-2-transfected 293 epithelial cells in nude mice.

Nude mice bearing HCCR-2H allografts display characteristics of an epithelial carcinoma. FIG. 25 shows hematoxylin-eosin staining of subcutaneous tumor nodules taken from the nude mice. The sections of the tumor nodules revealed typical epithelial cell nests separated by fibrous stroma.

EXAMPLE 13

Figure 26:
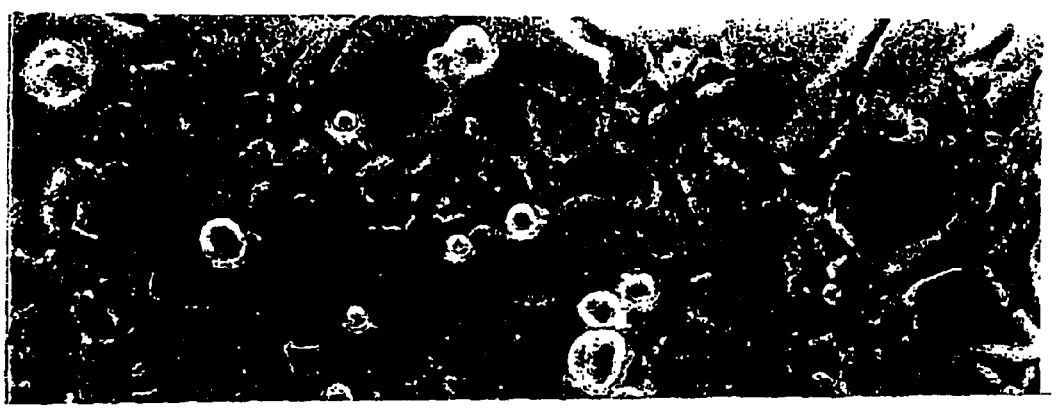
FIG. 26: phase-contrast features of monolayer-cultured nude mice-derived HCCR-2HN cells.

Establishment of New Cancer Cell Line from HCCR-2H Cell-induced Tumor Tissue The cells obtained from the tumor tissue of Example 12 was cultured in a conventional manner using 20% fetal bovine serum and the cultured cells were designated HCCR-2HN cells which have cytological features similar to HCCR-2H cells in vitro as shown in FIG. 26.

Figure 27:
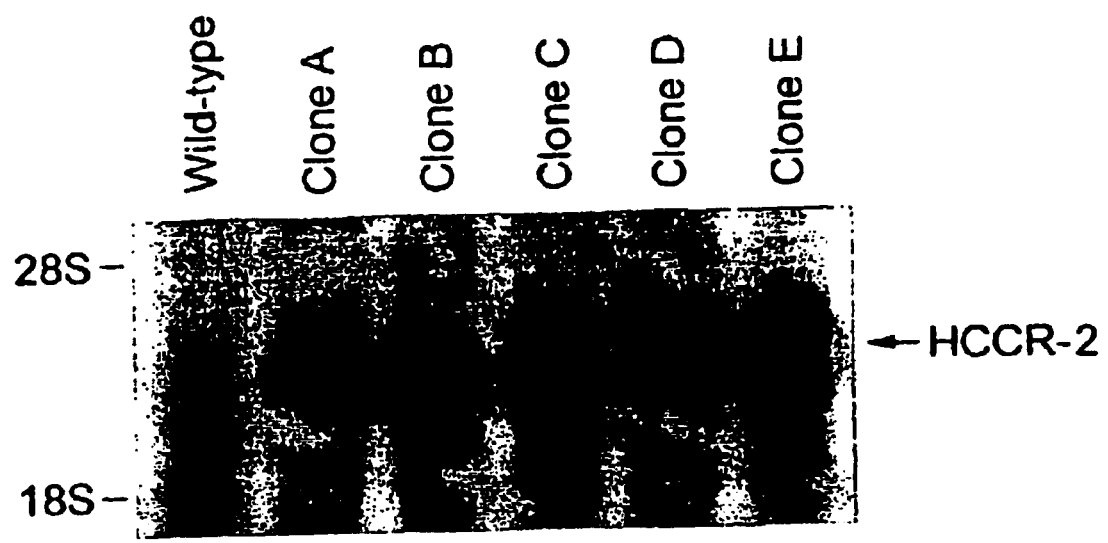
FIG. 27: the results of northern blot analyses for wild type 293 epithelial cell and HCCR-2-transfected 293 epithelial cells (clones A, B, C, D and E).

Further, northern blotting analyses for wild type 293 epithelial cell and HCCR-2-transfected 293 epithelial cells (clones A, B, C, D and E) were carried out. As shown in FIG. 27, HCCR-2 was transcribed at a high level in all 5 clones, while the expression of HCCR-2 gene is barely observable in wild type 293 epithelial cell.

While the embodiments of the subject invention have been described and illustrated, it is obvious that various changes and modifications can be made therein without departing from the spirit of the present invention which should be limited only by the scope of the appended claims.

What is claimed is:

1. A human cervical cancer 2 protooncogene having the nucleotide sequence of SEQ ID NO: 1.

2. A human cervical cancer 2 protooncogene having the nucleotide sequence comprising nucleotides Nos. 63 to 977 of SEQ ID NO:1 and encoding the amino acid sequence of SEQ ID NO: 2.

3. A vector comprising the protooncogene of claim 1.

4. A microorganism transformed with the vector of claim 3.

5. The microorganism of claim 4, which is E. coli JM109/HCCR2(Accession NO: KCTC 0668BP).

6. A process for preparing a protein having the amino acid sequence of SEQ ID NO: 2 comprising the step of culturing the microorganism of claim 4.

7. A kit for diagnosis of cancer which comprises the protooncogene of claim 1.

8. A process for preparing a protein having the amino acid sequence of SEQ ID NO: 2 comprising culturing the microorganism of claim 5.

9. A kit for diagnosing cancer which comprises the protooncogene of claim 2.

10. A vector comprising the protooncogene of claim 2.

11. A microorganism transformed with the vector of claim 10.

12. A process for preparing a protein having the amino acid sequence of SEQ ID NO: 2 comprising culturing the microorganism of claim 11.

* * * * *